(12) United States Patent
Vanover et al.

(10) Patent No.: US 9,956,227 B2
(45) Date of Patent: May 1, 2018

(54) METHOD FOR THE TREATMENT OF RESIDUAL SYMPTOMS OF SCHIZOPHRENIA

(71) Applicant: INTRA-CELLULAR THERAPIES, INC., New York, NY (US)

(72) Inventors: Kimberly Vanover, New York, NY (US); Peng Li, New Milford, NJ (US); Sharon Mates, New York, NY (US); Robert Davis, San Diego, CA (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days. days.

(21) Appl. No.: 15/101,874

(22) PCT Filed: Dec. 3, 2014

(86) PCT No.: PCT/US2014/068443
§ 371 (c)(1),
(2) Date: Jun. 3, 2016

(87) PCT Pub. No.: WO2015/085004
PCT Pub. Date: Jun. 11, 2015

(65) Prior Publication Data
US 2016/0310502 A1 Oct. 27, 2016

Related U.S. Application Data

(60) Provisional application No. 61/911,416, filed on Dec. 3, 2013, provisional application No. 61/925,607, filed on Jan. 9, 2014, provisional application No. 61/975,702, filed on Apr. 4, 2014, provisional application No. 62/032,326, filed on Aug. 1, 2014.

(51) Int. Cl.
| | |
|---|---|
| *A61K 45/06* | (2006.01) |
| *A61K 9/00* | (2006.01) |
| *A61K 31/4985* | (2006.01) |
| *A61K 31/5383* | (2006.01) |
| *A61K 9/51* | (2006.01) |

(52) U.S. Cl.
CPC ........ *A61K 31/5383* (2013.01); *A61K 9/0019* (2013.01); *A61K 9/0024* (2013.01); *A61K 9/5153* (2013.01); *A61K 31/4985* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,490,813 A | 12/1949 | Hughes et al. | |
| 3,299,078 A | 1/1967 | Pachter | |
| 3,813,392 A | 5/1974 | Sellstedt et al. | |
| 3,914,421 A | 10/1975 | Rajagopalan | |
| 4,001,263 A | 1/1977 | Plattner | |
| 4,115,577 A | 9/1978 | Rajagopalan | |
| 4,183,936 A | 1/1980 | Rajagopalan | |
| 4,219,550 A | 8/1980 | Rajagopalan | |
| 4,238,607 A | 12/1980 | Rajagopalan | |
| 4,389,330 A | 6/1983 | Tice et al. | |
| 4,522,944 A | 6/1985 | Doria et al. | |
| 4,530,840 A | 7/1985 | Tice et al. | |
| 4,971,971 A | 11/1990 | Tokunaga et al. | |
| 4,985,432 A | 1/1991 | Tokunaga et al. | |
| 5,114,976 A | 5/1992 | Norden | |
| 5,151,419 A | 9/1992 | Perenyi et al. | |
| 5,538,739 A | 7/1996 | Bodmer et al. | |
| 5,576,460 A | 11/1996 | Buchwald et al. | |
| 5,648,539 A | 7/1997 | Goodbrand et al. | |
| 5,648,542 A | 7/1997 | Goodbrand et al. | |
| 5,654,482 A | 8/1997 | Goodbrand et al. | |
| 5,705,697 A | 1/1998 | Goodbrand et al. | |
| 5,723,669 A | 3/1998 | Goodbrand et al. | |
| 5,723,671 A | 3/1998 | Goodbrand et al. | |
| 5,847,166 A | 12/1998 | Buchwald et al. | |
| 5,902,901 A | 5/1999 | Goodbrand et al. | |
| 6,043,370 A | 3/2000 | Kubo et al. | |
| 6,166,226 A | 12/2000 | Buchwald et al. | |
| 6,235,936 B1 | 5/2001 | Buchwald et al. | |
| 6,307,087 B1 | 10/2001 | Buchwald et al. | |

(Continued)

FOREIGN PATENT DOCUMENTS

| | | |
|---|---|---|
| EP | 0 058 481 | 8/1982 |
| EP | 0 856 508 | 8/1998 |

(Continued)

OTHER PUBLICATIONS

Rainer, M.K. in Neuropsychiatric Disease and Treatment 4(5), 919-927 (2008).*
"Securities" at http://securities.stanford.edu/filings-documents/1029/ALKS03-01/20031029_r01c_0312091.pdf (2003) (retrieved from the internet Jun. 13, 2017).*
Kay et al. in Schizophrenia Bulletin 13(2), 261-276 (1987).*
Alvir et al. Clozapine-Induced Agranulocytosis. The New England Journal of Medicine, 1993, vol. 329, No. 3, pp. 162-167.
Davis et al. "ITI-007 demonstrates brain occupancy at serotonin 5-HT2A and dopamine D2 receptors and serotonin transporters using positron emission tomography in healthy volunteers", Psychopharmacology, Published Online Apr. 25, 2016, pp. 601-614.
International Search Report of the International Searching Authority (US) dated Jul. 16, 2009 for corresponding International Application No. PCT/US2009/003261.

(Continued)

*Primary Examiner* — Dennis Heyer
(74) *Attorney, Agent, or Firm* — Hoxie & Associates LLC

(57) ABSTRACT

The disclosure provides the use of particular substituted heterocycle fused gamma-carboline compounds as pharmaceuticals for the treatment of residual symptoms of psychosis or schizophrenia. The disclosure also provides novel long acting injectable formulations of particular substituted heterocycle fused gamma-carboline compounds and use of such long acting injectable formulations for the treatment of residual symptoms of psychosis or schizophrenia.

25 Claims, 3 Drawing Sheets

(56) References Cited

U.S. PATENT DOCUMENTS

| | | |
|---|---|---|
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,465,693 B2 | 10/2002 | Buchwald et al. |
| 6,541,639 B2 | 4/2003 | Zhou et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 * | 7/2007 | Robichaud ............ C07D 221/18 514/229.5 |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,592,454 B2 | 9/2009 | Lee et al. |
| 7,614,727 B2 | 11/2009 | Hori |
| 7,645,752 B2 | 1/2010 | McDevitt et al. |
| 8,309,722 B2 | 11/2012 | Tomesch et al. |
| 8,309,772 B2 | 11/2012 | Weiner et al. |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,791,138 B2 | 7/2014 | Seeman et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 2001/0008942 A1 | 7/2001 | Buchwald et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0180875 A1 | 9/2004 | Lee et al. |
| 2004/0220178 A1 | 11/2004 | Robichaud et al. |
| 2005/0166771 A1 | 8/2005 | Gygi et al. |
| 2005/0222209 A1 | 10/2005 | Zeldis et al. |
| 2005/0239768 A1 | 10/2005 | Lee et al. |
| 2006/0128713 A1 | 6/2006 | Jolidon et al. |
| 2006/0178362 A1 | 8/2006 | Robichaud et al. |
| 2006/0205787 A1 | 9/2006 | Muller et al. |
| 2007/0203120 A1 | 8/2007 | McDevitt et al. |
| 2008/0069885 A1 | 3/2008 | Mesens et al. |
| 2008/0132552 A1 | 6/2008 | Kleinman et al. |
| 2008/0280941 A1 | 11/2008 | Lourtie et al. |
| 2009/0202631 A1 | 8/2009 | Yam et al. |
| 2010/0298382 A1 | 11/2010 | Seeman |
| 2011/0071080 A1 * | 3/2011 | Mates ..................... A61K 31/44 514/11.4 |
| 2011/0112105 A1 | 5/2011 | Tomesch et al. |
| 2014/0050783 A1 | 2/2014 | Mates et al. |
| 2014/0323491 A1 | 10/2014 | Tomesch et al. |
| 2014/0364609 A1 | 12/2014 | Tomesch et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2015/0166540 A1 | 6/2015 | Mates et al. |
| 2016/0031885 A1 | 2/2016 | Li et al. |
| 2016/0194325 A1 | 7/2016 | Tomesch et al. |
| 2017/0037048 A1 | 2/2017 | Mates et al. |
| 2017/0114037 A1 | 4/2017 | Davis et al. |
| 2017/0183350 A1 | 6/2017 | Mates et al. |
| 2017/0189398 A1 | 7/2017 | Mates et al. |

FOREIGN PATENT DOCUMENTS

| | | |
|---|---|---|
| EP | 0 976 732 | 2/2000 |
| EP | 1 245 553 | 10/2002 |
| EP | 1 254 884 | 11/2002 |
| EP | 1 564 671 | 1/2005 |
| EP | 1 539 115 | 6/2005 |
| GB | 1476087 | 6/1977 |
| GB | 2145422 | 3/1985 |
| WO | WO 1994/024125 | 10/1994 |
| WO | WO 1995/013814 | 5/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/059129 | 8/2002 |
| WO | WO 2002/085838 | 10/2002 |
| WO | WO 2004/010981 | 2/2004 |
| WO | WO 2004/013094 | 2/2004 |
| WO | WO 2004/039788 | 5/2004 |
| WO | WO 2004/056324 | 7/2004 |
| WO | WO 2006/034187 | 3/2006 |
| WO | WO 2006/081251 | 8/2006 |
| WO | WO 2007/025103 | 3/2007 |
| WO | WO 2007/084841 | 7/2007 |
| WO | WO 2008/112280 | 9/2008 |
| WO | WO 2009/017836 | 2/2009 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |

OTHER PUBLICATIONS

Rye (Sleep Disorders and Parkinson's Disease, 2000, accessed online http://www.waparkinsons.org/edu_research/articles/Sleep_Disorders.html), 2 pages.

U.S. Appl. No. 62/015,120, filed Jun. 20, 2014, Mates et al.

U.S. Appl. No. 61/975,502, filed Apr. 4, 2014, Mates et al.

U.S. Appl. No. 62/009,849, filed Jun. 9, 2014, Davis et al.

U.S. Appl. No. 61/975,610, filed Apr. 4, 2014, Mates et al.

U.S. Appl. No. 15/629,481, filed Jun. 21, 2017, Li et al.

Avendano, C., et al., "The problem of the existence of C(Ar)-H . . . N Intramolecular Hydrogen Bonds in a Family of 9-Azaphenyl-9H-carbazoles," *J. Chem. Soc. Perkin Trans.*, vol. 2, pp. 1547-1555, (1993).

Balbach, S., et al., "Pharmaceutical evaluation of early development candidates 'the 100 mg-approach'", International Journal of Pharmaceutics, vol. 275, p. 1-12 (2004).

Bastin, R., et al.,"Salt Selection and Optimisation Procedures for Pharmaceutical New Chemical Entities", Organic Process and Research Development, vol. 4, No. 5, pp. 427-435 (2000).

(56) References Cited

OTHER PUBLICATIONS

Beletskaya, I.P., et at, "Pd- and Cu-catalyzed selective arylation of benzotriazole," *Tetrahedron Letters*, vol. 39, pp. 5617-5620, (1998).
Berger, J., et al., "Synthesis of some conformationally restricted analogs of fentanyl." *Journal of Medicinal Chemistry*, vol. 20, No. 4, p. 600-602. 1977.
Boger, D., et al., "Inverse Electron Demand Diels-Alder Reactions of Heterocyclic Aza Dienes. Studies on the Toal Synthesis of Lavendamycin: Investigative Studies on the Preparation of the CDE β-Carboline Ring System and AB Quinoline-5,8-quinone Ring System" J. Org. Chem., vol. 50, p. 5782-5789, (1985).
Bowman, W.R., et al., "Copper (1) Catalysed Aromatic Nucleophilic Substitution: A Mechanistic and Synthetic Comparison with the $S_{RN}1$ Reaction", Tetrahedron Letters, vol. 25(50) p. 5821-5824, (1984).
Bowman, W.R., et al.,"Synthesis of 1H-quinazoline-4-ones using intramolecular aromatic nucelophilic substitution," *ARKIVOC*, vol. x, pp. 434-442 (2003).
Bowman, W.R., et al., "Intramolecular Aromatic Substitution ($S_{RN}1$) Reactions—Use of Entrainment for the Preparation of Benzothiazoles," *Tetrahedron Letters*, vol. 23, pp. 5093-5096, (1982).
Bowman, W.R., et al., "Copper(1) Catalysed Aromatic Nucleophilic Substitution: A Mechanistic and Synthetic Comparison with the $S_{RN}1$ Reaction," *Tetrahedron Letters*, vol. 25, pp. 5821-5824, (1984).
Bremner et al., "Neuroimaging of Posttraumatic Stress Disorder", Psychiatric Annals Journal, vol. 28, Issue 8, p. 445-450, (1998).
Bryan-Lluka, L. J. et al., "Potencies of haloperidol metabolites as inhibitors of the human noradrenaline, dopamine and serotonin transporters in transfected COS-7 cells", *Naunyn-Shemiedeberg's Arch Pharmacol*, 1999, vol. 360, pp. 109-115.
Byrn, S., et al., "Pharmaceutical Solids: A Strategic Approach to Regulatory Considerations", Pharmaceutical Research, vol. 12, No. 7, p. 945-954 (1995).
Crawford, K., et al., "Copper-Catalyzed amidations of bromo substituted furans and thiophenes", Tetrahedron Letters, vol. 43, p. 7365-7368, (2002).
Darmani, N. A., et al., "Do Functional Relationships Exist Between 5-$HT_{1A}$ and 5-$HT_2$ Receptors?," *Pharmacology and Biochemistry & Behavior*, vol. 36, p. 901-906, (1990).
Evindar, G., et al., "Copper- and Palladium-Catalyzed Intramolecular Aryl Guanidinylation: An Efficient Method for the Synthesis of 2-Aminobenzimidazoles", *Organic Letters*, vol. 5, No. 2, p. 133-136, (2003).
Ezquerra, J., et al., "Efficient Reagents for the Synthesis of 5-, 7-, and 5, 7-Substitued Indoles Starting from Aromatic Amines: Scope and Limitations", J. Org. Chem., vol. 61, p. 5804-5812, (1996).
Fawcett, J., "Posttraumatic Stress Disorder, Stress, and Happiness", Psychiatric Annals Journal, vol. 28, Issue 8, p. 427-428, (1998).
Fee, W.W., et al., "Copper (II)-promoted solvolyses of nickel (II) complexes III. Tetradentate Schiff base ligands containing various diamine segments," *Aust. J. Chem.*, vol. 26, pp. 1475-1485, (1973).
Ferreira, I., et al., "Novel synthetic routes to thienocarbazoles via palladium or copper catalyzed amination or amidation of arylhalides and intramolecular cyclization", Tetrahedron, vol. 58, p. 7943-7949, (2002).
Finet, J-P., et al., "Recent advances in ullmann reaction: copper (II) diacetate catalysed N-, )- and S-arylation involving polycoordinate heteroatomic derivatives," *Current Organic Chemistry*, vol. 6, pp. 597-626, (2002).
Foster, P.S., et al., "Acetylcholinesterase inhibitors reduce spreading activation in dementia," *Neuropsychologia*, vol. 50, p. 2093-2099, (2012).
Friedman, M.J.., "Current and Future Drug Treatment for Post-traumatic Stress Disorder Patients", *Psychiatric Annals Journal*, vol. 28, Issue 8, p. 464-468, (1998).
Goodbrand, H.B., et al., "Ligand-Accelerated catalysis of the Ullmann condensation: Application to hole conducting triarylamines," *J. Org. Chem.*, vol. 64, pp. 670-674, (1999).

Grant, D., "Theory and Origin and Polymorphism", Polymorphism in Pharmaceutical Solids, Chapter 1, p. 1-10 (1999).
Guillory, J.K., "Generation of Polymorphs, Hydrates, Solvates, and Amorphous Solids", Polymorphism in Pharmaceutical Solids, Chapter 5, p. 183-226 (1999).
Hackam, D., et al., "Translation of Research Evidence from Animals to Humans", JAMA, vol. 296(14), p. 1731-1732 (2006).
Hamann, B., et al., "Systematic Variation of Bidentate Ligands used in Aryl Halide Amination. Unexpected Effects of Steric, Electronic, and Geometric Perturbations", *J. Am. Chem. Soc.*, vol. 120, p. 3694-3703, (1998).
Harbert, C.A. et al., "Neuroleptic Activity in 5-Aryltetrahydro-γ-carbolines", *J. Med. Chem.*, vol. 23, pp. 635-643 (1980).
Hartwig, J., "Palladium-catalyzed amination of aryl halides: Mechanism and rational catalyst design," *Synlett*, pp. 329-340, (1996).
Harvey, B.H., et al., "Serotonin and Stress: Protective or Malevolent Actions in the Biobehavioral Response to Repeated Trauma?" Annals of the New York Academy of Sciences, vol. 1032, p. 267-272; DOI: 10.1196/annals.1314.035 (2004).
Hassan, J., et al., "Aryl-aryl bond formation one century after the discovery of the ullmann reaction," *Chem. Rev.*, vol. 102, pp. 1359-1469, (2002).
Haynes, "Occurrence of Pharmaceutically Acceptable Anions and Cations in the Cambridge Structural Database", *Journal of Pharmaceutical Sciences*, vol. 94, No. 10, p. 2111-2120 (2005).
International Preliminary Report on Patentability for International Application No. PCT/US2013/036514 dated Oct. 14, 2014.
International Search Report issued in International Application No. PCT/US2008/003340, dated Aug. 8, 2008, 3 pages.
International Search Report issued in International Application No. PCT/US2009/001608, dated Apr. 27, 2009, 3 pages.
International Search Report issued in International Application No. PCT/US2011/00719, dated Jul. 5, 2011, 3 pages.
International Search Report issued in International Application No. PCT/US2013/036512, dated Aug. 19, 2013, 4 pages.
International Search Report issued in International Application No. PCT/US2013/036514, dated Aug. 16, 2013, 3 pages.
International Search Report issued in International Application No. PCT/US2013/036515, dated Aug. 13, 2013, 3 pages.
Ito, T., et al., "Studies of organic catalytic reactions. VI. The function of pyridine and copper in the Rosenmund-von Braun reaction," *Bulletin of the Chemical Society of Japan* vol. 41, pp. 419-423, (1968).
Izrayelit, L., "Schizoaffective Disorder and PTSD Successfully Treated With Olanzapine and Supportive Psychotherapy", Psychiatric Annals Journal, vol. 28, Issue 8, p. 424-426, (1998).
Jain et al., "Polymorphism in Pharmacy", Indian Drugs, 23(6), 315-316 (1986).
Ji, J., et al., "Selective amination of polyhalopyridines catalyzed by a palladium-xantphos complex," *Organic Letters*, vol. 5, No. 24, pp. 4611-4614, (2003).
Jordan, V.C., "Tamoxifen: A Most Unlikely Pioneering Medicine", Nature Reviews: Drug Discovery, vol. 2, p. 205-213, (2003).
Kametani, T., et al., "A Novel Synthesis of Indole Derivatives", *Heterocycles*, vol. 14 (3), p. 277-280, (1980).
Kang, S-K., et al., "Copper-catalyzed N-arylation of aryl iodides with benzamides or nitrogen heterocycles in the presence of ethylendiamine," *Synlett*, No. 3, pp. 427-430, (2002).
Kay, S.R., et al., "The Positive and Negative Syndrome Scale (PANSS) for Schizophrenia," *Schizophrenia Bulletin*, vol. 13, Issue 2, pp. 261-276, (1987).
Kessler, R.C., et al., "Lifetime Prevalence and Age-of-Onset Distributions of DSM-IV Disorders in the National Comorbidity Survey Replication", Arch Gen Psychiatry; vol. 62, p. 593-602, (2005).
Khorana, N., et al., "Gamma-Carbolines: Binding at 5-HT5A Serotonin Receptors", *Bioorganic & Medicinal Chemistry*, vol. 11, Issue 5, 6, pp. 717-722, p. 718 Table 1, (2003).
Kiyomori, A., et al., "An efficient copper-catalyzed coupling of aryl halides with imidazoles," *Tetrahedron Letters*, vol. 40, pp. 2657-2660, (1999).
Klapars, A., et al., "A general and efficient copper catalyst for the amidation of aryl halides and the N-arylation of nitrogen heterocycles," *J. Am. Chem. Soc.*, vol. 123, pp. 7727-7729, (2001).

(56) References Cited

OTHER PUBLICATIONS

Klapars, A., et al., "A general and efficient copper catalyst for the amidation of aryl halides," *J. Am. Chem. Soc.*, vol. 124, pp. 7421-7428, (2002).

Kondratov, S.A., et al., "Nucelophilic substitution in the aromatic series. Lv. Reaction of o-nitrochlorobenzene with ammonia in the presence of copper compounds," *Zhurnal Organidreskoi Khimii*, vol. 51(11), pp. 2387-2390, (1979).

Koppel, J., et al., "Optimal Treatment of Alzheimer's Disease Psychosis: Challenges and Solutions," *Neuropsychiatric Disease and Treatment*, vol. 10, pp. 2253-2262, (2014).

Kwong, F.Y., et al., "Mild and efficient copper-catalyzed amination of aryl bromides with primary alkylamines," *Organic Letters*, vol. 5, No. 6, pp. 793-796, (2003).

Lebert, F., et al., "Trazodone in Fronto-Temporal Dementia", *Research and Practice in Alzheimer's Disease*, vol. 11, 356-360, (2006).

Lee, T., et al. "Novel, Highly Potent, Selective 5-HT$_{2A}$/D$_2$ Receptor Antagonists as Potential Atypical Antipsychotics," *Bioorg. Med. Chem. Lett.* vol. 13, pp. 767-770, (2003).

Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).

Lieberman, J.A., et al., "ITI-007 for the Treatment of Schizophrenia: A 4-Week Randomized, Double-Blind, Controlled Trial," *Biol. Psychiatry*, 79(12), pp. 952-961, (2015).

Lin, Y-T., et al., "Dosage and Duration of Antipsychotic Treatment in Demented Outpatients with Agitation or Psychosis," *Journal of the Fomosan Medical Association*, vol. 114, pp. 147-153, (2015).

Lipschitz, D.S., et al., "Childhood Posttraumatic Stress Disorder: A Review of Neurobiologic Sequelae", Psychiatric Annals Journal, vol. 28, Issue 8, p. 452-457, (1998).

Lopez, et al., "Psychiatric Symptoms Vary with the Severity of Dementia in Probably Alzheimer's Disease," *J. Neuropsychiatry Clin. Neurosc.*, vol. 15(3), pp. 346-353, (2003).

Louie, J., et al., "Palladium-Catalyzed Synthesis of Arylamines from Aryl Halides, Mechanistic Studies lead to Coupling in the Absence of Tin Reagents", *Tetrahedron Letters*, vol. 36(21), p. 3609-3612, (1995).

Lounkine, E., et al.,"Formal Concept Analysis for the Identification of Molecular Fragment Combinations Specific for Active and Highly Potent Compounds," *J. Med. Chem.*, vol. 51, No. (17), 5342-5348, (2008).

Madhusoodanan, S., et al., "Pharmacological Management of Behavioral Symptoms Associated with Dementia," *World J. Psychiatr.*, vol. 4, No. 4, pp. 72-79, (2014).

March et al, Advanced Organic Chemistry; Reactions, Mechanisms and Structures, Fourth Edition, pp. 910-911 (1992).

Marcoux, J-F., et al., "A general copper-catalyzed synthesis of diaryl ethers," *J. Am. Chem. Soc.*, vol. 119, pp. 10539-10540, (1997).

Mohamed, S., et al., "Pharmacotherapy of PTSD in the U.S. Department of Veterans Affairs: diagnostic- and symptom-guided drug selection", *J. Clin. Psychiatry*, vol. 69, pp. 959-965, (2008).

Morgan, C.A., et al., "Acoustic Startle in Individuals With Posttraumatic Stress Disorder", Psychiatric Annals Journal, vol. 28, Issue 8, p. 430-434, (1998).

Mulrooney, C., et al., "Recent developments in copper-catalyzed n-arylation with aryl halides," Essay—University of Pennsylvania (2004).

Murakami et al., "Fischer Indolization of Ethyl Pyruvate 2-[2-(Trifluoromethyl) phenyl]-phenylhydrazone and New Insight into the Mechanism of the Goldberg Reaction." *Chem. Pharm. Bull*, vol. 43(8), p. 1281-1286, (1995).

Nagai, Y., et al., "Synthesis of 2,3,4,4a,5,9b-hexahydro-1H-pyrido[4,3-b] indole derivatives and their central nervous system activities." *Journal of Medicinal Chemistry*, vol. 22, No. 6, p. 677-683. 1979.

Newman, A.W., et al., "Solid-state analysis of the active pharmaceutical ingredient in drug products", *Drug Discovery Today*, vol. 8, No. 9, 898-903 (2003).

Pond, S.M. et al., "Stereospecific reduction of haloperidol in human tissues". *Biochemical Pharmacology*, vol. 44 (5), p. 867-871 (1992).

Protective Groups in Organic Synthesis, Third Edition, John Wiley & Sons, Inc., p. 494-505, (1999).

Rackova, L., et al., "Free Radical Scavenging and Antioxidant Activities of Substituted Hexahydropyridoindoles. Quantitative Structure-Activity Relationships." *Journal of Medicinal Chemistry*, vol. 49, No. 8, p. 2543-2548, (2006).

Sadighi, J.P., et al., "A highly active palladium catalyst system for the arylation of anilines," *Tetrahedron Letters*, vol. 39, pp. 5327-5330, (1998).

Savjani, K., et al., "Drug Solubility: Importance and Enhancement Techniques", International Scholarly Research Network Pharmaceutics, vol. 2012, pp. 1-10, (2012).

Sigel, H., et al., "Tenary Complexes in Solution", *Inorganic Chemistry*, vol. 13, No. 2, p. 462-465 (1974).

Singhal, D., et al., "Drug polymorphism and dosage form design: a practical perspective", *Advanced Drug Delivery Reviews*, vol. 56, pp. 335-347 (2004).

Skoog, D., et al., "Principles of Instrumental Analysis, $4^{th}$ Edition", p. 577 (1992).

Smith, A.D., et al., "Oxford Dictionary of Biochemistry and Molecular Biology", Oxford University Press, p. 145, (1997).

Snyder, G.L., et al., "Functional profile of a novel modulator of serotonin, dopamine, and glutamate neurotransmission," *Psychopharmacology*, vol. 232, p. 605-621 (2015) Published online Aug. 2014, DOI 10.1007/s00213-014-3704-1.

Southwick, S.M., et al., "Neuroendocrine Alterations in Post-traumatic Stress Disorder", Psychiatric Annals Journal, vol. 28, Issue 8, p. 436-442, (1998).

Sugahara, M., et al., "A Facile Copper-Catalyzed Ullman Condensation: N-Arylation of Heterocyclic Compounds Containing an-NHCO-Moiety", *Chem. Pharm. Bull.*, vol. 45(4), p. 719-721, (1997).

Taragano, F.E., et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).

Wagaw, S., et al., "A palladium-catalyzed method for the preparation of indoles via the Fischer indole synthesis," *Journal of the American Chemical Society*, vol. 121, No. 44, pp. 10251-10263, (1999).

Weschules, D., et al., "Acetylcholinesterase Inhibitor and N-Methyl-D-Aspartic Acid Receptor Antagonist Use among Hospice Enrollees with a Primary Diagnosis of Dementia", *Journal of Palliative Medicine*, vol. 11, No. 5, 738-745 (2008).

Wiese, M., "DSC Detection of Polymorphism in Pharmaceutical Anhdrous Dexamethasone Acetate," *TA Instruments*, TA302:1-4 (2002).

Wolfe, J.P., et al., "An improved catalyst system for aromatic carbon-nitrogen bond formation: The possible involvement of bis(phosphine) palladium complexes as key intermediates," *JACS*, vol. 118, pp. 7215-7216, (1996).

Wolfe, J.P., et al., "Intramolecular palladium-catalyzed aryl amination and aryl amidation," *Tetrahedron*, vol. 52, No. 21, pp. 7525-7546, (1996).

Wolter, M., et al., "Synthesis of N-aryl hydrazides by copper-catalyzed coupling of hydrazides with aryl iodides," *Organic Letters*, vol. 3, No. 23, pp. 3803-3805, (2001).

Written Opinion of the International Searching Authority for International Application No. PCT/US2013/036514 dated Aug. 16, 2013, 4 pages.

Yamada, K., et al., "A mild copper-mediated intramolecular amination of aryl halides," *Synlett*, No. 2, pp. 231-234, (2002).

Yang, B.H., "The development of efficient protocols for the palladium-catalyzed cyclization reactions of secondary amides and carbamates," *Organic Letters*, vol. 1, No. 1, pp. 35-37, (1999).

(56) References Cited

OTHER PUBLICATIONS

Yudofsky, S., et al., "Propranolol in the Treatment of Rage and Violent Behavior in Patients with Chronic Brain Syndromes", Am. J. Psychiatry, vol. 138, p. 218-220, (1981).
Zhang, Z., et al., "Highly efficient copper-catalyzed N-arylation of alkylamines with aryl iodides using phosphoramidite as ligand", Catalysis Communications, vol. 6, p. 784-787, (2005).

* cited by examiner

PANSS Negative Symptom Sub-Scale for patients subgroup with prominent negative symptoms at baseline Total PANSS in sub-group of patients with depression at baseline PANSS Negative Symptom Sub-scale in sub-group of patients with depression at baseline Prosocial PANSS Factor Change from Baseline compared to Placebo

* $p \leq 0.05$ versus Placebo;  $p < 0.01$ versus Placebo; * $p < 0.001$ versus Placebo

METHOD FOR THE TREATMENT OF RESIDUAL SYMPTOMS OF SCHIZOPHRENIA

CROSS-REFERENCE TO RELATED APPLICATIONS

This application is a U.S. National Stage application of PCT/US2014/068443, filed on Dec. 3, 2014, which claims priority from U.S. Provisional Application Nos. 61/911,416 filed on Dec. 3, 2013; 61/925,607 filed on Jan. 9, 2014; 61/975,702 filed on Apr. 4, 2014; and 62/032,326 filed on Aug. 1, 2014, the contents of each of which are incorporated by reference in their entirety.

TECHNICAL FIELD

The present invention relates to use of particular substituted heterocycle fused gamma-carbolines as described herein, in free or pharmaceutically acceptable salt forms, as pharmaceuticals and pharmaceutical compositions as primary or adjunct therapy in the treatment of acute and residual phases of schizophrenia, particularly including the treatment of residual symptoms such as active social avoidance, passive social withdrawal, emotional withdrawal, anxiety, tension, stereotyped thinking, and somatic concerns. The compounds disclosed herein can be used to treat both acute symptoms and residual symptoms that appear during acute exacerbations but define the residual phase of the illness, e.g., schizophrenia, once the acute symptoms wane. Therefore, the compounds disclosed herein can be used alone or in combination with other antipsychotic medications as well as other active agents that treat co-morbid disorders such depression and/or sleep disorders. As the response profile across symptoms associated with schizophrenia may be particularly beneficial in improving social function, the compounds disclosed herein can be used to improve social integration and social function. Such a response profile can be beneficial to prodromal, exacerbation and residual phases of schizophrenia.

BACKGROUND OF THE INVENTION

Psychosis, particularly schizophrenia affects 1.1% of the population worldwide. This illness comprises three phases: prodromal phase, active phase and residual phase. Prodromal phase is an early phase wherein subclinical signs and symptoms are observed. These symptoms may include loss of interest in usual pursuits, withdrawal from friends and family members, confusion, trouble with concentration, feeling of listless and apathy. Active phase is characterized by exacerbations of positive symptoms such as delusions, hallucinations and suspiciousness. Residual phase is characterized by negative symptoms such as emotional withdrawal, passive social withdrawal, and stereotyped thinking, and symptoms of general psychopathology including active social avoidance, anxiety, tension, and somatic concerns. Residual phase symptoms are often accompanied by depression, cognitive dysfunction and insomnia. Collectively, these residual phase symptoms are not well-treated by many antipsychotic drugs currently available on the market and therefore are usually observed after the active phase symptoms have subsided after treatment. This phase of the illness is when patients would like to return to more productive and fulfilling lives, but since the residual negative symptoms and cognitive impairment are not properly treated, this goal is frustrated. There remains an urgent need for anti-psychotic agents, which can treat not just the active or acute phase symptoms, but also the residual phase symptoms of psychosis, e.g., schizophrenia.

Substituted heterocycle fused gamma-carbolines are known to be agonists or antagonists of 5-HT$_2$ receptors, particularly 5-HT$_{2A}$ and 5-HT$_{2C}$ receptors, in treating central nervous system disorders. These compounds have been disclosed in U.S. Pat. Nos. 6,548,493; 7,238,690; 6,552,017; 6,713,471; U.S. RE39680, U.S. RE39679, U.S. Pat. Nos. 7,183,282 and 7,071,186, as novel compounds and medical use for the treatment of disorders associated with 5-HT$_{2A}$ receptor modulation such as obesity, anxiety, depression, psychosis, schizophrenia, sleep disorders, sexual disorders, migraine, autism, conditions associated with cephalic pain, social phobias, and gastrointestinal disorders such as dysfunction of gastrointestinal tract motility. PCT/US08/03340 and U.S. application Ser. No. 10/786,935 also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, WO 2009/145900, WO 2011/133224, WO 2013/155505, WO 2013/155504 and WO 2013/155506 teach further substituted heterocyclic fused gamma-carboline compounds and/or their use for the treatment of one or more disorders involving the 5-HT$_{2A}$, serotonin transporter (SERT) and/or dopamine D1/D2 pathways.

Although the above-cited references pertaining to substituted heterocyclic fused gamma-carboline compounds teach treatment of certain disorders associated with psychosis and/or depression, none of these references disclose treatment of residual symptoms of psychosis, particularly residual symptoms of schizophrenia.

SUMMARY OF THE INVENTION

It has been discovered that particular substituted heterocycle fused gamma-carboline compounds (the compounds described herein below) possess mechanisms of action that are believed to have the potential to yield a first-in-class antipsychotic therapy. The Compounds of Formula I combine potent serotonin 5-HT$_{2A}$ receptor antagonism, dopamine receptor phosphoprotein modulation, or DPPM, glutamatergic modulation and serotonin reuptake inhibition into a single drug candidate for the treatment of acute and residual schizophrenia. At dopamine D2 receptors, the Compounds of Formula I have dual properties and act as both post-synaptic antagonists and pre-synaptic partial agonists. The Compounds of Formula I also stimulate phosphorylation of glutamatergic NMDA NR2B, or GluN2B, receptors in a mesolimbic specific manner. It is believed that this regional selectivity in the brain areas thought to mediate the efficacy of antipsychotic drugs, together with serotonergic, glutamatergic, and dopaminergic interactions, may result in antipsychotic efficacy for positive, negative, affective and cognitive symptoms associated with schizophrenia. The serotonin reuptake inhibition could allow for antidepressant activity for the treatment of schizoaffective disorder, co-morbid depression, and/or as a stand-alone treatment for major depressive disorder. It is believed that the Compounds of Formula I may also be useful for the treatment of bipolar disorder and other psychiatric and neurodegenerative disorders, particularly behavioral disturbances associated with dementia, autism and other CNS diseases. These features of the Compounds of Formula I may be able to improve the quality of life of patients with schizophrenia and enhance social function to allow them to more fully integrate into their families and their workplace. In addition, the Compounds of Formula I may be shown to treat disorders at either low-doses (e.g., sleep, aggression and agitation) or high-doses (e.g., acute exacerbated and residual schizophrenia, bipolar disorders, and mood disorders).

As the compounds described below are effective in treating not just acute symptoms, but also residual symptoms of psychosis, the invention therefore provides, in one aspect, methods of using the particular substituted heterocycle fused gamma-carboline compounds (the compounds described herein below), either alone or as an adjunctive therapy for the treatment of the residual symptoms of psychosis, particularly schizophrenia. This is a new and unexpected utility.

Thus, the present invention is directed to a method (Method A) for the treatment of residual symptoms comprising administering to a patient in need thereof an effective amount of the Compound of Formula I:

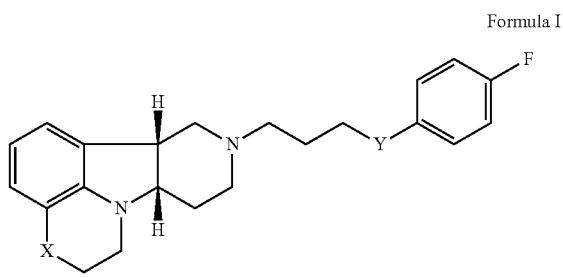

Formula I wherein:
X is —O—, —NH— or —N(CH$_3$)—;
Y is —O—, —C(R$_2$)(OH)—, —C(R$_3$)(OR$_1$) or —C(O)—;
R$_1$ is C$_{1-6}$alkyl (e.g., methyl) or a physiologically hydrolysable and acceptable acyl, e.g., selected from —C(O)—C$_{1-21}$alkyl (e.g., —C(O)—C$_{1-5}$alkyl, —C(O)—C$_{6-15}$ alkyl or —C(O)—C$_{16-21}$alkyl), for example wherein R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl, or —C(O)—C$_{15}$alkyl e.g., wherein such compound hydrolyzes to provide a natural or unnatural, saturated or unsaturated fatty acid of formula R$_1$—OH and a Compound of Formula 1 wherein Y is —C(R$_2$)(OH)—, e.g., wherein the compound hydrolyzes to form the hydroxy Compound of Formula I wherein Y is —C(R$_2$)(OH)— on the one hand and octanoic acid, decanoic acid, dodecanoic acid, tetradecanoic acid or hexadecanoic acid on the other hand);
R$_2$ is H or —C$_{1-6}$alkyl (e.g., methyl); and
R$_3$ is H or —C$_{1-6}$alkyl (e.g., methyl);
e.g., wherein "alkyl" refers to a straight chain hydrocarbon moiety, optionally saturated or unsaturated and optionally substituted with one or more hydroxy or C$_{1-22}$alkoxy (e.g., ethoxy) groups;
in free or pharmaceutically acceptable salt form.

In a further embodiment, the compound of Formula I of Method A is a compound wherein:
X is —O—, —NH— or —N(CH$_3$)—;
Y is —O—, —C(H)(OH)—, —C(H)(OR$_1$) or —C(O)—; and
R$_1$ is a physiologically hydrolysable and acceptable acyl, e.g., selected from —C(O)—C$_{1-21}$alkyl (e.g., —C(O)—C$_{1-5}$alkyl, —C(O)—C$_{6-15}$alkyl or —C(O)—C$_{16-21}$alkyl), for example wherein R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl, or —C(O)—C$_{15}$alkyl e.g., wherein such compound hydrolyzes to provide a natural or unnatural, saturated or unsaturated fatty acid of formula R$_1$—OH and a Compound of Formula I wherein Y is —C(R$_2$)(OH)—, e.g., wherein the compound hydrolyzes to form the hydroxy Compound of Formula I wherein Y is —C(R$_2$)(OH)— on the one hand and octanoic acid, decanoic acid, dodecanoic acid, tetradecanoic acid or hexadecanoic acid on the other hand);
e.g., wherein "alkyl" refers to a straight chain hydrocarbon moiety, optionally saturated or unsaturated and optionally substituted with one or more hydroxy or C$_{1-22}$alkoxy (e.g., ethoxy) groups;
in free or pharmaceutically acceptable salt form.

In a further embodiment, the patient of Method A is suffering from residual symptoms of psychosis, for example, schizophrenia (e.g., residual sub-type), delusional disorder (e.g., somatic type), major depression with psychosis, bipolar disorder with psychotic symptoms, brief psychotic disorder, schizophreniform disorder, schizoaffective disorder or psychosis caused by a medical condition or substance use. Preferably, the patient is suffering from residual symptoms of schizophrenia.

In another further embodiment, the residual phase symptoms include: negative symptoms such as blunted affect, emotional withdrawal, poor rapport, passive or apathetic social withdrawal, difficulty in abstract thinking, lack of spontaneity and flow of conversation and stereotyped thinking; general psychopathology symptoms such as somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance; cognitive impairment and sleep disorders (e.g., insomnia) In a particular embodiment. Method A treats residual symptoms (negative, effective and cognitive symptoms) associated with schizophrenia.

In another further embodiment, the effective amount of the Compound of Formula I is about 1 mg to about 140 mg per dose per day, in another embodiment, about 2.5 mg to about 120 mg, in another embodiment about 10 mg to about 120 mg per dose per day, in another embodiment, about 60 mg to about 120 mg per dose per day, in still another embodiment, about 10 mg to about 60 mg per dose per day, in another embodiment, about 20 mg to about 60 mg per dose per day, in still another embodiment, about 20 mg, about 40 mg, or about 60 mg per dose per day. The compounds of the current invention are effective in treating both the positive symptoms, which occur during active or acute phase of psychosis (e.g., effective in treating positive symptoms such as delusions and hallucinations) as well as negative and other residual symptoms generally observed in the residual phase. Preferably, the effective amount for the treatment of acute and residual symptoms of schizophrenia is about 60 mg per day. In particular embodiment, the dosages disclose herein for oral administration are based on the amount of the Compounds of Formula I in acid addition salt form, particularly toluene sulfonic acid addition salt form.

Therefore, the invention provides methods as follows:
1.1 Method A comprising a compound of Formula I, wherein X is —N(CH$_3$);
1.2 Method A comprising a compound of Formula I, wherein X is —NH;

1.3 Method A comprising a compound of Formula I, wherein X is O;

1.4 Method A or any of 1.1-1.3, comprising a compound of Formula I, wherein Y is —C(O)—;

1.5 Method A or any of 1.1-1.3, comprising a compound of Formula I, wherein Y is —O—;

1.6 Method A or any of 1.1-1.3 comprising a compound of Formula I, wherein Y is —C($R_2$)(OH)—, e.g., —C(H)(OH)—;

1.7 Method A or any of 1.1-1.3 comprising a compound of Formula I, wherein Y is —C($R_3$)($OR_1$), e.g., —C(H)($OR_1$);

1.8 Method A or formula 1.7, wherein $R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand);

1.9 Method A or formula 1.7, wherein $R_1$ is —C(O)—$C_{6-15}$alkyl, e.g., —C(O)—$C_9$alkyl;

1.10 Method A or formula 1.7, wherein $R_1$ is —C(O)—$C_{1-5}$alkyl, e.g., —C(O)—$C_3$alkyl;

1.11 Method A or formula 1.7, wherein $R_1$ is —$C_{1-6}$alkyl (e.g., methyl);

1.12 Method A or any of formula 1.1-1.11, wherein $R_2$ is H or —$C_{1-6}$alkyl (e.g., methyl);

1.13 Method A or any of formula 1.1-1.11, wherein $R_2$ is H;

1.14 Method A or any of formula 1.1-1.11, wherein $R_2$ is —$C_{1-6}$alkyl (e.g., methyl);

1.15 Method A or any of formula 1.1-1.11, wherein $R_3$ is H or —$C_{1-6}$alkyl (e.g., methyl);

1.16 Method A or any of formula 1.1-1.11, wherein $R_3$ is H;

1.17 Method A or any of formula 1.1-1.11, wherein $R_3$ is —$C_{1-6}$alkyl (e.g., methyl);

1.18 any of the preceding methods wherein the Compound of Formula I is selected from a group consisting of a compound of Formula I wherein:
X is —O— and Y is —C(H)(OH)—,
X is —NH— and Y is —C(H)(OH)—,
X is —N($CH_3$)— and Y is —C(H)(OH)—,
X is —O— and Y is —C(O)—,
X is —O— and Y is —O—,
X is —N($CH_3$)— and Y is —C(O)—,
X is —N($CH_3$)— and Y is —O—,
X is —NH— and Y is —C(O)—,
X is —NH— and Y is —O—,
X is —N($CH_3$)— and Y is —C(H)($OR_1$),
X is —NH— and Y is —C(H)($OR_1$), or
X is —O— and Y is —C(H)($OR_1$);
X is —O— and Y is —C($CH_3$)(OH)—,
X is —NH— and Y is C($CH_3$)(OH)—,
X is —N($CH_3$)— and Y is C($CH_3$)(OH)—, 1.19 any of the preceding methods wherein X is —O— and Y is —C(O)— in the Compound of Formula I;

1.20 any of the preceding methods wherein X is —NH— and Y is —C(H)(OH)— in the Compound of Formula I;

1.21 any of the preceding methods wherein X is —N($CH_3$)— and Y is —C(H)(OH)— in the Compound of Formula I is;

1.22 any of the preceding methods wherein X is —O— and Y is —C(O)— in the Compound of Formula I;

1.23 any of the preceding methods wherein X is —O— and Y is —O— in the Compound of Formula I;

1.24 any of the preceding methods wherein X is —N($CH_3$)— and Y is —C(O)— in the Compound of Formula I;

1.25 any of the preceding methods wherein X is —O— and Y is —C(H)(OH)— in the Compound of Formula I 1.26 any of the preceding methods wherein X is —NH— and Y is —C(H)(OH)— in the compound of Formula I;

1.27 any of the preceding methods wherein X is —N($CH_3$)— and Y is —C(H)(OH)— in the compound of Formula I;

1.28 any of the preceding methods wherein X is —N($CH_3$)— and Y is —C(H)($OR_1$) and $R_1$ is —C(O)—$C_{1-21}$ alkyl in the compound of Formula I;

1.29 any of the preceding methods wherein X is —N(H)— and Y is —C(H)($OR_1$) and $R_1$ is —C(O)—$C_{1-21}$ alkyl in the compound of Formula I;

1.30 any of the preceding methods wherein X is —O— and Y is —C(H)($OR_1$) and $R_1$ is —C(O)—$C_{1-21}$alkyl in the compound of Formula I;

1.31 Any of the preceding methods, wherein the Compound of Formula I is a compound of Formula IA:

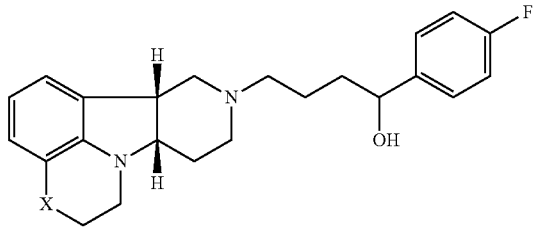

1.32 Any of the preceding methods, wherein the Compound of Formula I is a compound of Formula IB:

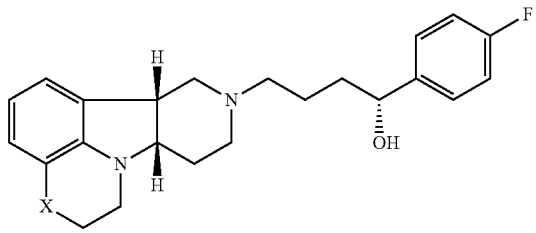

1.33 Any of the preceding methods, wherein the Compound of Formula I is a compound of Formula IC:

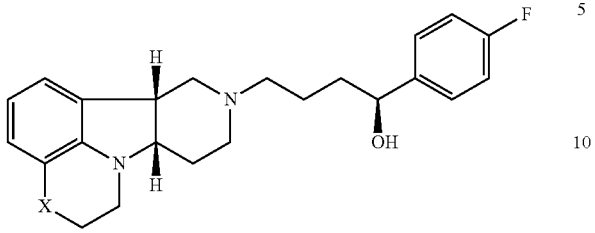

1.34 Any of the preceding methods, wherein the Compound of Formula I is a compound of Formula ID (sometimes referred to herein as Compound B):

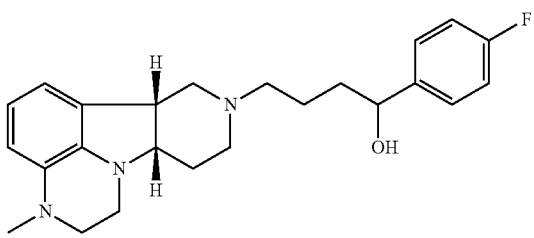 [SMILES: CN1CCN2c3c(cccc31)[C@@H]1CN(CCCC(O)c3ccc(F)cc3)CC[C@@H]12]

1.35 Any of the preceding methods, wherein the Compound of Formula I is a compound of Formula IE (sometimes referred to herein as Compound A):

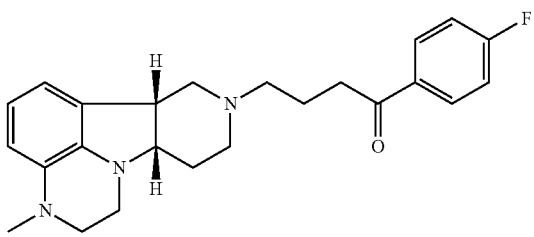 [SMILES: CN1CCN2c3c(cccc31)[C@@H]1CN(CCCC(=O)c3ccc(F)cc3)CC[C@@H]12]

1.36 Any of the preceding methods, wherein the Compound of Formula I is a compound of Formula IF:

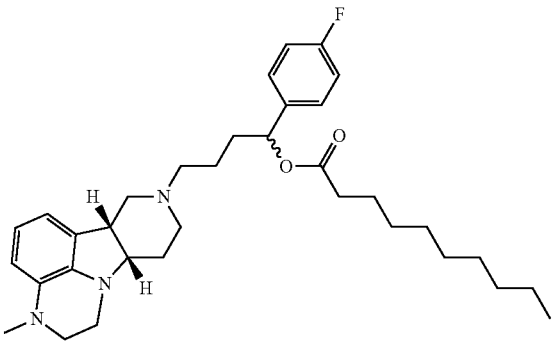 [SMILES: CCCCCCCCCC(=O)OC(CCCN1CC[C@H]2[C@@H](C1)c1cccc3c1N2CCN3C)c1ccc(F)cc1]

1.37 Any of the preceding methods, wherein the Compound of Formula I is a compound of Formula IG:

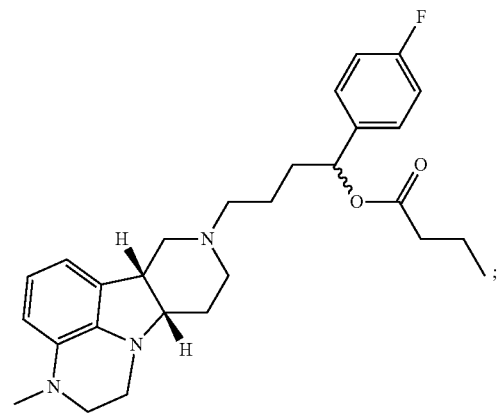 [SMILES: CCCC(=O)OC(CCCN1CC[C@H]2[C@@H](C1)c1cccc3c1N2CCN3C)c1ccc(F)cc1]

1.38 Any of the foregoing methods wherein the Compound of Formula I is administered orally, for example in once a day in a single daily dose or twice a day in a divided dose, for example in the form of a tablet or capsule.

1.39 Any of the foregoing methods wherein the effective amount of the Compound of Formula I is a daily oral dosage of 10-120 mg/day, e.g., about 60 mg of the p-toluene sulfonic acid addition salt of the Compound of Formula IE:

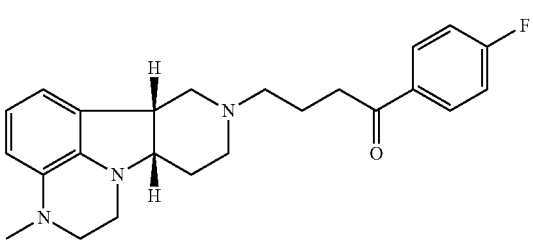 [SMILES: CN1CCN2c3c(cccc31)[C@@H]1CN(CCCC(=O)c3ccc(F)cc3)CC[C@@H]12]

1.40 Any of the foregoing methods wherein the Compound of Formula I is administered as a sustained release injectable form, e.g., an injectable depot form, e.g., administered once or twice a month, e.g., in the form of a bioerodable microparticle, e.g., the Compound of Formula IE:

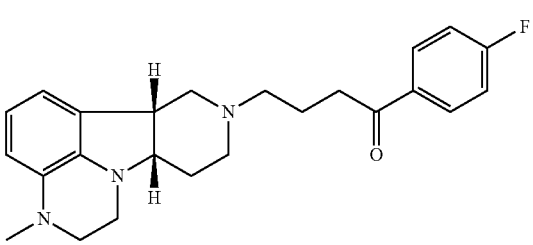 [SMILES: CN1CCN2c3c(cccc31)[C@@H]1CN(CCCC(=O)c3ccc(F)cc3)CC[C@@H]12]

e.g., in free base form.

1.41 Any of the foregoing methods comprising administering a long acting injectable formulation of a Compound of Formula I, e.g., Composition 2, e.g., any of Compositions 2.1, et seq. as set forth below.

1.42 Any of the foregoing methods further comprising administering one or more other therapeutic agents such as additional antipsychotic agents and/or antidepressant agents and/or hypnotic agents;

1.43 Method 1.38, wherein the one or more other therapeutic agents are selected from anti-depressive agents such as compounds that modulate GABA activity (e.g., enhances the activity and facilitates GABA transmission), a GABA-B receptor agonist, a 5-HT modulator (e.g., a 5-HT$_{1A}$ receptor agonist, a 5-HT$_{2A}$ receptor antagonist, a 5-HT$_{2A}$ receptor inverse agonist, etc.), a melatonin receptor agonist, an ion channel modulator (e.g., blocker), a serotonin-2 receptor antagonist/reuptake inhibitor (SARIs), an orexin receptor antagonist, an H3 receptor agonist, a noradrenergic receptor antagonist, a galanin receptor agonist, a CRH receptor antagonist, human growth hormone, a growth hormone receptor agonist, estrogen, an estrogen receptor agonist, a neurokinin-1 drug; and antipsychotic agents, e.g., atypical antipsychotic agents, in free or pharmaceutically acceptable salt form;

1.44 Method 1.42 or 1.43, wherein the one or more other therapeutic agents are antipsychotic agents, e.g., chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, cariprazine, amisulpride, zotepine, sertindole, wherein the one or more other therapeutic agents are administered as an adjunct to the compound of Formula I or the compound of Formula I is an adjunct to the one or more other therapeutic agents;

1.45 Any of the foregoing methods, wherein the effective amount is 1 mg to 120 mg per day or 10 mg to 120 mg per day, or 10 mg to 60 mg per day, or 10 mg to 40 mg per day, or 1 mg to 10 mg per day, or 10 mg per day, 20 mg per day, 40 mg per day or 60 mg per day; In a particular embodiment, the effective amount of the Compound of Formula I disclosed in this formula is based on the amount of the Compound of Formula I in an acid addition salt, non-prodrug form, e.g., in toluenesulfonic acid addition salt, non-prodrug form.

1.46 Method A or any of 1.38-1.45, wherein the one or more other therapeutic agents are anti-depressive agents, e.g., one or more antidepressants selected from selective serotonin reuptake inhibitors (SSRIs)(e.g., selected from citalopram, escitalopram oxalate, fluoxetine, fluvoxamine maleate, paroxetine, sertraline, dapoxetine), serotonin-norepinephrine reuptake inhibitors (SNRIs)(e.g., selected from venlafaxine, desvenlafaxine, duloxetine, milnacipran, levomilnacipran, sibutramine), and tricyclic antidepressants; triple reuptake inhibitors, anxiolytics, busperone, and trazadone;

1.47 Methods 1.45 wherein compound of Formula I is administered as an adjunct to one or more other therapeutic agents such as SSRI anti-depressive agents or the SSRI anti-depressive agents are administered as an adjunct to the compound of Formula I;

1.48 The method of 1.47, wherein said one or more antidepressant agents are selected form SSRI's such as citalopram (Celexa, Cipramil, Emocal, Sepram, Seropram), escitalopram oxalate (Lexapro, Cipralex, Esertia), fluoxetine (Prozac, Fontex, Seromex, Seronil, Sarafem, Fluctin (EUR)), fluvoxamine maleate (Luvox, Faverin), paroxetine (Paxil, Seroxat, Aropax, Deroxat, Paroxat), sertraline (Zoloft, Lustral, Serlain), dapoxetine; in free or pharmaceutically acceptable salt form;

1.49 Any of the foregoing methods, wherein the compound of Formula I is administered as part of a long-acting injectable microsphere composition;

1.50 The method of 1.49, wherein the long-acting injectable microsphere composition is a composition according to any one of 2.1 to 2.22 herein below.

In a particular embodiment of Method A et seq., the patient is a patient who has not responded or has not responded adequately to treatment with another antipsychotic agent, e.g., chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, cariprazine, amisulpride, zotepine, sertindole. Therefore, the compound of Formula I may be administered as a primary therapy or an adjunct therapy, e.g., adjunct to another antipsychotic agent.

In another aspect, the invention provides a method (Method B) for the treatment of any of the following disorders: schizoaffective disorder, co-morbid depression, major depressive disorder, bipolar disorder (e.g., bipolar I and/or bipolar II disorder), Autism Spectrum disorder (e.g., autistic disorder, Asperger's disorder, Pervasive developmental disorder not otherwise specified (PDD-NOS), Rett's disorder (Rett syndrome), childhood disintegrative disorder) comprising administering to a patient in need thereof an effective amount of a Compound of Formula I, in free or pharmaceutically acceptable salt form. In a particular embodiment, the disorder of Method B is bipolar disorder (e.g., bipolar I and/or bipolar II disorder). In another particular embodiment, the disorder of Method B is Autism Spectrum disorder. In still another particular embodiment, the disorder of Method B is major depressive disorder.

Therefore, depending on the combination of disorders to be treated, the Compounds of Formula I may be used strategically. For example at lower doses (for example, a daily oral dose of 1-10 mg, e.g., 1 mg, 5 mg and 10 mg of the Compound of Formula I in toluenesulfonic acid addition salt form), the Compounds of Formula I are useful for the treatment of sleep disorder, aggression and agitation, Alzheimer's disease and other dementias, Autism Spectrum disorder, Parkinson's disease and Intermittent Explosive Disorder (IED). At higher dose (for example, a daily oral dose of 60 mg of the Compound of Formula I in toluenesulfonic acid addition salt form), the Compounds of Formula I are useful for treating acute exacerbated and residual schizophrenia, bipolar depression, major depressive disorder, generalized anxiety disorder. At very high dose (for example a daily oral dose of 120 mg of the Compound of Formula I in toluenesulfonic acid addition salt form), morning administration may produce somnolence/sedation. Therefore, at such higher daily doses, administration in the evening is preferable.

The Compounds of Formula I may exist in free or salt form, e.g., as acid addition salts. In this specification unless otherwise indicated language such as "Compounds of Formula I", "antipsychotic agents", "anti-depressive agents", "other therapeutic agents", and the like is to be understood as embracing the compounds in any form, for example free or acid addition salt form, or where the compounds contain acidic substituents, in base addition salt form. The Compounds of Formula I are intended for use as pharmaceuticals, therefore pharmaceutically acceptable salts are preferred. Salts which are unsuitable for pharmaceutical uses may be useful, for example, for the isolation or purification of free Compounds of Formula I or their pharmaceutically acceptable salts, are therefore also included. Pharmaceutically acceptable salts include, for example, the hydrochloride, mesylate and tosylate salts. Preferably, the Compounds of Formula I, particularly wherein X is —N(CH$_3$)— and Y is —C(O)—, are in tosylate (toluenesulfonic acid addition) salt form. Where dosage amounts of salts are given by weight, e.g., milligrams per day or milligrams per unit dose, the dosage amount of the salt may be based on the weight of the corresponding free base or as otherwise indicated. In a particular embodiment, the dosage of the Compounds of Formula I in acid addition salt form for oral administration is based on the weight of the toluenesulfonic acid addition salt form, not the free base form. For example, in a particular embodiment, the 10 mg, 60 mg, 120 mg dosage amount of the Compound of Formula I is based respectively, on 10 mg, 60 mg and 120 mg of the Compound of Formula I in toluenesulfonic acid addition salt form, not based on the amount of the free base. For example, 60 mg dosage of the compound for oral administration of Compounds of Formula I (e.g., wherein X is —N(CH$_3$)— and Y is —C(O)—) in toluene sulfonic acid addition salt form refers to the compound in tosylate salt form, which is equivalent to approximately 41.7 mg of said compound in free base form.

The invention also provides the foregoing methods, e.g., Method A, e.g., any of 1.1-1.50, and Method B, wherein the Compound of Formula I, in free or pharmaceutically acceptable salt form is administered in a composition, wherein said Compound of Formula I in free or pharmaceutically acceptable salt form is in admixture or in association with a pharmaceutically acceptable diluent or carrier.

In a particular embodiment, the invention also provides the foregoing methods, e.g., Method A, e.g., any of 1.1-1.50, and Method B, wherein the Compound of Formula I, in free or pharmaceutically acceptable salt form is administered in an immediate release or sustained or delayed release formulation, e.g., depot formulation.

In one embodiment, the sustained or delayed release formulation comprises the Compounds of Formula I disclosed herein (e.g., the compound of formula I or any of those described in any of formulae 1.1-1.50) in a polymeric matrix. In another embodiment, the Compounds of Formula I are dispersed or dissolved within the polymeric matrix. In a further embodiment, the polymeric matrix comprises standard polymers used in depot formulations such as polymers selected from a polyester of a hydroxy fatty acid and derivatives thereof, or a polymer of an alkyl alpha-cyano-acrylate, a polyalkylene oxalate, a poly(ortho) ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 75:25, PLGA 85:15 and PLGA 90:10 polymer. In another embodiment, the polymer is selected from poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a particular embodiment, the polymeric matrix comprises poly (d,l-lactide-co-glycolide). The Compound of Formula I in a polymeric matrix may be in admixture or in association with a pharmaceutically acceptable diluent or carrier.

The sustained or delayed release formulations as hereinbefore described are particularly useful for sustained or delayed release, wherein the Compounds of Formula I are released upon degradation of the polymeric matrix. These formulations may release the Compounds of Formula I over a period of up to 180 days, e.g., from about 14 to about 30 to about 180 days. For example, the polymeric matrix may degrade and release the Compounds of Formula I over a period of about 30, about 60 or about 90 days. In another example, the polymeric matrix may degrade and release the Compounds of Formula I over a period of about 120, or about 180 days.

In still another further embodiment, the sustained or delayed release formulation is formulated for administration by injection.

For example, the disclosure provides long-acting injectable (LAI) formulations of Compounds of Formula I. Such LAIs may be optimized as to carrier composition, particle size, molecular weight of carrier, loading of active ingredient, and dosage, e.g., as described in the examples. In addition to convenience of administration, and ensuring patient compliance, LAI formulations of Compounds of Formula I surprisingly provide advantages as to pharmacokinetics and side effects. When a Compound of Formula I is administered using an LAI formulation, as opposed to an oral dosage form, the first pass metabolism in the liver is avoided, meaning that a lower proportion of Compound of Formula I is metabolized before reaching the brain. Sustained or delayed release formulations as described herein generally impart fewer extrapyramidal side effects, and offer better tolerability and reduced total dose than the corresponding immediate release formations. Sustained or delayed release formulations, and particularly long-acting injectable formulations, allow a patient to achieve and maintain therapeutically effective levels of drug in the CNS while receiving a much lower total dosage than would be needed to achieve the same body level of drug using immediate release oral formulations. For long-acting injectable formulations in particular, this effect is partly due to the avoidance of the first-pass metabolism that occurs with oral medications, including oral sustained and delayed release medications.

The effective amount of the Compound of Formula I when administered as a long-acting injectable formulation is therefore found to be much lower than the effective amount when administered orally, e.g., from about 100 mg per month to about 600 mg per month, and preferably from 150 mg per month to 300 mg per month.

In a particular embodiment, therefore, the disclosure provides a long-acting injectable formulation (Composition 2) comprising polymeric microspheres, wherein the microspheres comprise:
  a poly(D,L-lactide-co-glycolide) polymer (PLGA) polymer matrix and
  an effective amount of a Compound of Formula I, as hereinbefore described, in free or pharmaceutically acceptable salt form, the Compound of Formula I being dispersed, dissolved or encapsulated in the polymer matrix.

For example, the disclosure provides:
2.1 Composition 2, wherein the PLGA polymer is about 75:25 PLA/PLG with either carboxylic acid or carboxylic ester end groups.
2.2 Composition 2 or 2.1, wherein the PLGA polymer is about 75:25 PLA/PLG with carboxylic acid end groups.
2.3 Composition 2, 2.1 or 2.2, wherein the Compound of Formula I is in free base form.

2.4 Any foregoing Composition wherein the Compound of Formula I is selected from Compounds of Formula IA, IB, IC, ID, IE.

2.5 Any foregoing Composition wherein the Compound of Formula I is the Compound of Formula IE:

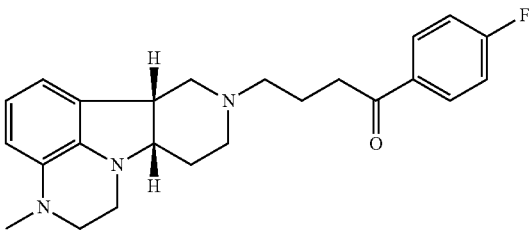 [SMILES: CN1CCN2c3c(cccc31)[C@@H]1CN(CCCC(=O)c3ccc(F)cc3)CC[C@@H]12]

e.g., in free base form.

2.6 Any of the foregoing Compositions, wherein the Compound of Formula I is a compound of Formula ID:

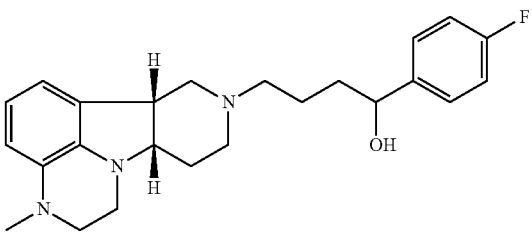 [SMILES: CN1CCN2c3c(cccc31)[C@@H]1CN(CCCC(O)c3ccc(F)cc3)CC[C@@H]12]

e.g., in free base form.

2.7 Any foregoing Composition wherein the average molecular weight range for the PLGA polymer is, for example 20 kD to 200 kD, for example, 24,000 to 38,000 daltons, or about 113,000 daltons or about 159,000 daltons.

2.8 Any foregoing Composition wherein the time frame for complete degradation of the microspheres and release of the encapsulated drug compounds is, e.g., less than 6 months, less than 4 months, less than 3 months, less than 2 months, or less than 1 month.

2.9 Any foregoing Composition wherein the diameter of the microspheres, e.g., the average diameter (or $D_{50}$), the 10$^{th}$ percentile diameter ($D_{10}$), the 25$^{th}$ percentile diameter ($D_{25}$), the 75$^{th}$ percentile diameter ($D_{75}$), or the 90$^{th}$ percentile diameter ($D_{90}$), is from about 10 µm to about 200 µm, for example, from about 20 µm to about 160 µm, or from about 20 µm to about 120 µm, or from about 20 µm to about 100 µm, or from about 20 µm to about 80 µm, or from about 20 µm to about 70 µm, or from about 20 µm to about 60 µm, or from about 20 µm to about 50 µm, or from about 20 µm to about 40 µm, or from about 20 µm to about 30 µm, or from about 25 µm to about 70 µm, or from about 25 µm to about 60 µm, or from about 25 µm to about 50 µm, or from about 25 µm to about 40 µm, or from about 30 µm to about 60 µm, or from about 30 to 50 µm, or from about 30 µm to about 40 µm, or from about 30 µm to about 120 µm, or from about 40 µm to about 120 µm, or from about 40 µm to about 100 µm, or from about 40 µm to about 80 µm, or from about 40 µm to about 70 µm, or from about 40 µm to about 60 µm, or from about 40 µm to about 50 µm, or from about 50 µm to about 100 µm, or from about 50 µm to about 80 µm, or from about 50 µm to about 70 µm, or from about 50 µm to about 60 µm, or from about 60 µm to about 100 µm, or from about 60 µm to about 90 µm, or from about 60 µm to about 80 µm, or from about 60 µm to about 70 µm, or from about 70 µm to about 100 µm, or from about 70 µm to about 90 µm, or from about 70 µm to about 80 µm, or from about 75 µm to about 110 µm, or from about 40 µm to about 160 µm, or from about 50 µm to about 160 µm, or from about 50 µm to about 120 µm, or about 20 µm, about 30 µm, about 40 µm, about 50 µm, about 60 µm, about 70 µm, about 80 µm, about 90 µm, or about 100 µm.

2.10 Any foregoing Composition wherein the diameter of the microspheres, e.g., the average diameter (or $D_{50}$), the 10$^{th}$ percentile diameter ($D_{10}$), the 25$^{th}$ percentile diameter ($D_{25}$), the 75$^{th}$ percentile diameter ($D_{75}$), or the 90$^{th}$ percentile diameter ($D_{90}$), is from 10 µm to 160 µm, for example, 20 µm to 70 µm, 25 µm to 70 µm, 40 to 120 µm, or 20 µm to 60 µm, or 20 µm to 50 µm, 30 µm to 60 µm, 30 to 50 µm, 40 µm to 50 µm, or about 30 µm, or about 40 µm, or about 50 µm.

2.11 Any foregoing Composition wherein the amount of the Compound of Formula I dispersed, dissolved or encapsulated in each microsphere, on average, is from about 5% by weight to about 50% by weight, for example, from about 10% by weight to about 50% by weight, or from about 20% by weight to about 40% by weight, or from about 30% by weight to about 40% by weight, or, for example, about 8.5% by weight, or about 16% by weight, or about 30% by weight, or about 35% by weight, or about 40% by weight.

2.12 Any foregoing Composition wherein the inherent viscosity is about 0.1 to about 1, for example about 0.3 to about 0.4, about 0.7, about 0.8, about 0.9 dL/g.

2.13 Any of the foregoing Compositions for use in Method A, e.g. any of Methods 1.1 et seq. or in Method B, as hereinbefore described.

2.14 Any of the foregoing Compositions for use in patients who have difficulty adhering to a regular treatment regimen, either intentionally or unintentionally.

2.15 Any of the foregoing Compositions for administration to patients on a weekly, biweekly or monthly basis, or once every 2, 3 4, 5 or 6 months.

2.16 Any of the foregoing Compositions for intramuscular, intraperitoneal, intrathecal, epidural, or subcutaneous injection, e.g. subcutaneous or intramuscular injection, e.g., intramuscular injection.

2.17 Any of the foregoing Compositions for intramuscular injection.

2.18 Any of the foregoing Compositions, further comprising an antioxidant, e.g., in an amount effective to inhibit or reduce oxidation of the Compound of Formula 1.

2.19 Any of the foregoing Compositions further comprising an antioxidant, wherein the antioxidant is a water-soluble antioxidant (e.g., ascorbic acid, lipoic acid), or a lipid-soluble antioxidant (e.g., lipoic acid, vitamin E, tocopherols, carotenes or phenolic antioxidants), or a neutral or weakly basic antioxidant, or a catalytic antioxidant (e.g., ebselen), or a metal-containing antioxidant.

2.20 Any of the foregoing Compositions further comprising an antioxidant, wherein the antioxidant is a lipidic or neutral or weakly basic antioxidants, e.g., wherein the polymer comprises carboxy end groups.

2.21 Any of the foregoing Compositions, further comprising an antioxidant, wherein the anti-oxidant is a phenolic antioxidant (e.g., butylated hydroxyanisole (BHA) or butylated hydroxytoluene (BHT)).

2.22 Any of the foregoing Compositions, further comprising an antioxidant, wherein the anti-oxidant is BHT.

In still another embodiment, the invention provides Methods A or B as hereinbefore described wherein the Compound of Formula I is formulated in an osmotic controlled release oral delivery system (OROS) for delivery of the Compounds of Formula I, e.g., analogous to the systems described in WO 2000/35419 and EP 1 539 115 (U.S. Pub. No. 2009/0202631), the contents of each of which applications are incorporated by reference in their entirety. Therefore in one embodiment, the invention provides Methods A or B as hereinbefore described, wherein the compound of Formula I is formulated in a device comprising (a) a gelatin capsule containing the Compound of Formula I, in free or pharmaceutically acceptable salt form, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Composition P.1)

In still another embodiment, the invention provides Methods A or B as hereinbefore described wherein the compound of Formula I is formulated in a composition comprising a gelatin capsule containing a liquid, the Compounds of Formula I, in free or pharmaceutically acceptable salt form as hereinbefore described, the gelatin capsule being surrounded by a composite wall comprising a bather layer contacting the external surface of the gelatin capsule, an expandable layer contacting the barrier layer, a semi-permeable layer encompassing the expandable layer, and an exit orifice formed or formable in the wall. (Composition P.2)

In still another embodiment, the invention provides Methods A or B as hereinbefore described wherein the compound of Formula I is formulated in a composition comprising a gelatin capsule containing a liquid, the Compound of Formula I, in free or pharmaceutically acceptable salt form as hereinbefore described, the gelatin capsule being surrounded by a composite wall comprising a bather layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Composition P.3)

In still another embodiment, the invention provides a composition comprising a gelatin capsule containing a liquid, the Compound of Formula I, in free or pharmaceutically acceptable salt form as hereinbefore described, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Composition P.4). The expandable layer may be formed in one or more discrete sections, such as for example, two sections located on opposing sides or ends of the gelatin capsule.

In a particular embodiment, the Compounds of Formula I in the Osmotic-controlled Release Oral delivery System (i.e., in Composition P.1-P.4) as hereinbefore described are in a liquid formulation, which formulation may be neat, liquid active agent, liquid active agent in a solution, suspension, emulsion or self-emulsifying composition or the like.

Further information on Osmotic-controlled Release Oral delivery System compositions including characteristics of the gelatin capsule, barrier layer, expandable layer, semipermeable layer, and orifice may be found in WO 2000/35419, the contents of which are incorporated by reference in their entirety. Other Osmotic-controlled Release Oral delivery Systems may be found in EP 1 539 115 (U.S. Pub. No. 2009/0202631), the contents of which are incorporated by reference in their entirety.

In still another embodiment, the invention provides Methods A or B as hereinbefore described wherein the compound of formula I is formulated in a device comprising (a) two or more layers, said two or more layers comprising a first layer and a second layer, said first layer comprising the Compound of Formula I, in free or pharmaceutically acceptable salt form as herein before described, said second layer comprising a polymer; (b) an outer wall surrounding said two or more layers; and (c) an orifice in said outer wall. (Composition P.5)

Composition P.5 preferably utilizes a semi-permeable membrane surrounding the three-layer-core described herein: in these embodiments the first layer is referred to as a first drug layer and contains low amounts of drug (e.g., the Compounds of Formula I) and an osmotic agent such as a salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Composition P.6)

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent to the exit orifice; and a second drug layer located within the compartment between the first drug layer and the expandable layer, the drug layers comprising the Compound of Formula I in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of a salt, e.g., sodium chloride. The delivery profile from the core is dependent on the weight, formulation and thickness of each of the drug layers. (Composition P.7)

In a particular embodiment, Composition P.7 comprises the first drug layer comprising salt and the second drug layer containing no salt. Composition P.5-P.7 may optionally comprise a flow-promoting layer between the membrane and the drug layers. Compositions P.1-P.7 will generally be referred to as Osmotic-controlled Release Oral delivery System Composition.

The invention further provides a pharmaceutical composition as hereinbefore described comprising a Compound of Formula I in free or pharmaceutically acceptable salt form, e.g., as described in any of Methods A or 1.1-1.50, or Method B in admixture with a pharmaceutically acceptable diluent or carrier, e.g., in an immediate or sustained or delayed release formulation, including a long-acting injectable formulation, for use in the treatment of residual symptoms as described in any of Methods A, or 1.1-1.50, or for use in the treatment of the disorders as described in Method B.

In another aspect, the invention provides use of the Compound of Formula I or the pharmaceutical composition comprising the compound of Formula I in free or pharmaceutically acceptable salt form as described in Methods A or 1.1-1.50, formulated in an immediate release or sustained or delayed release formulation, including a long-acting injectable formulation, as hereinbefore described, (in the manufacture of a medicament) for the treatment of residual symptoms as described in any of Methods A or 1.1-1.50, or for the treatment of the disorders as described in Method B.

In another aspect, the invention provides use of the Compound of Formula I or any pharmaceutical composition as hereinbefore described (e.g., Compositions P.1 to P.7 or Composition 2) comprising the Compound of Formula I in free or pharmaceutically acceptable salt form as described in Methods A or 1.1-1.50, wherein the compound is in admixture or association with an antioxidant. Without being bound by any particular theory, it is believed that the presence of an antioxidant within the composition will stabilize the compound of Formula I. In a preferred embodiment, the long acting injectable microspheres contain an antioxidant, wherein it is believed that the antioxidant will stabilize the compound of Formula I during release from the microsphere.

DETAILED DESCRIPTION OF THE INVENTION

Figure 1:
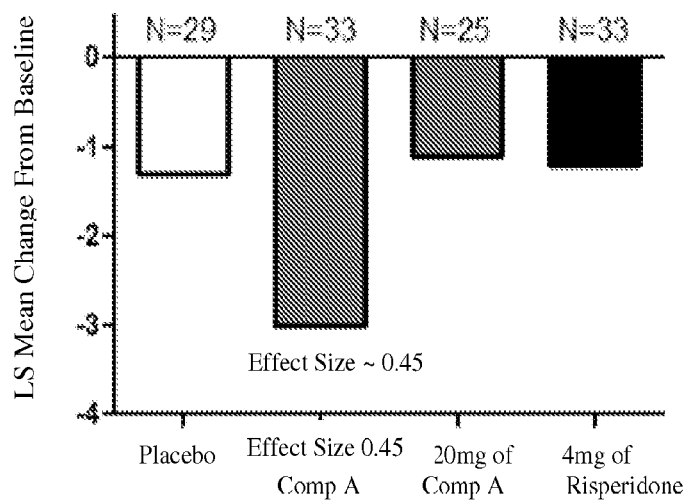
FIG. 1: PANSS Negative Symptom Sub-Scale for patients subgroup with prominent negative Symptoms at baseline.

The current invention provides an unmet need in the treatment of not only acute symptoms, but also residual symptoms of psychosis, particularly schizophrenia. Patients suffering from schizophrenia are currently treated with either conventional or atypical antipsychotic agents. These agents, which may be effective in treating positive symptoms of psychosis, generally are inadequate for treating residual symptoms. Thus, a different or additional treatment is needed to improve outcomes. In one embodiment, the methods of the present invention use a compound of Formula I alone as hereinbefore described, or used in a combination of the compound of Formula I and one or more different antipsychotic agents for the treatment of residual symptoms and acute symptoms of psychosis.

As used herein "residual symptoms" include negative symptoms and general psychopathology symptoms as described in the Positive and Negative Symptom Scale (PANSS) for Schizophrenia described in Kay et al., Schizophr. Bull. (1987) 13(2):261-276, the contents of which are incorporated by reference in their entirety. Negative symptoms include: blunted affect, emotional withdrawal, poor rapport, passive/apathetic social withdrawal, difficulty in abstract thinking, lack of spontaneity and flow of conversation and stereotyped thinking. General psychopathology symptoms include: somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance. Residual symptoms may also include depression, cognitive impairment and sleep disorders (e.g., insomnia) Of these residual symptoms, the Compounds of Formula I are particularly useful for the treatment of passive social withdrawal, stereotyped thinking, somatic concerns, anxiety, tension, active social avoidance and depression. Most patients with schizophrenia exhibit deficits in social function preventing successful reintegration into society. Social function deficits can be measured using the PANSS-Derived Prosocial factor. Prosocial factor is comprised of items from the Positive, Negative and General Psychopathology subscales such as active social avoidance, emotional withdrawal, passive social withdrawal, stereotyped thinking, hallucinatory behavior and suspiciousness. This factor is shown to be sensitive to change in the clinical trial setting. Since the Compounds of Formula I, particularly Compound A as defined in Example 1, reduce negative symptoms and also treat several other symptom domains, it is believed that the Compounds of Formula I may be useful in treating social function deficits. Therefore, the compounds of the present invention are particularly useful in improving social integration and social function in patients suffering from schizophrenia. Social function is the ability to recognize, understand, process and use external cues to solve problems, maintain work performance and conduct interpersonal relationships.

Treatment of these residual symptoms is also particularly effective in schizophrenic patients also suffering from depression. 60 mg of the Compound of Formula I, particularly Compound A as defined in Example 1 in toluenesulfonic acid addition salt form, administered once daily in the morning improves symptoms associated with schizophrenia measured by a statistically significant and clinically meaningful decrease in the PANSS total score after 28 days of treatment. This compound A also does not cause hyperprolactinemia, EPS/akathisia, weight gain or cardiovascular safety issues. At the same dosage, this compound A also statistically significantly improves the positive symptom subscale and the general psychopathology subscale of the PANSS. Further, the Compound of Formula I, particularly Compound A as defined in Example 1 in toluenesulfonic acid addition salt form at 60 mg improves negative symptoms in a subgroup of patients with prominent negative symptoms at baseline. Significantly, it also improves certain items on the negative symptom and general psychopathology subscales consistent with improved social function.

The term "acute symptoms" of psychosis or schizophrenia refers to positive symptoms of the PANSS such as delusions, conceptual disorganization, hallucinatory behavior and suspiciousness.

The term "psychosis" refers to illnesses such as schizophrenia, delusional disorder, major depression with psychosis, bipolar disorder with psychotic symptoms, brief psychotic disorder, schizophreniform disorder, schizoaffective disorder or psychosis caused by a medical condition or substance use. Preferably, the patient suffering from residual symptoms of psychosis is a patient suffering from residual symptoms of schizophrenia.

The term "bipolar disorder" refers to a disorder characterized by extreme shifts in mood. Individuals with bipolar disorder may experience intense feelings of over-excitement, irritability, and impulsivity with grandiose beliefs and racing thoughts, referred to as a manic episode. Symptoms of depression may include feeling tired, hopeless and sad, with difficulty concentrating and thoughts of suicide. Some people experience both types of symptoms in the same "mixed" episode. Severe symptoms of bipolar disorder can be associated with hallucinations or delusions, otherwise referred to as psychosis.

The words "treatment" and "treating" are to be understood accordingly as embracing prophylaxis and treatment or amelioration of symptoms of disease and/or treatment of the cause of the disease.

The term "patient" may include a human or non-human patient.

If not otherwise specified or clear from context, the following terms herein have the following meanings:

(i) "Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

Methods of Making Compounds of Formula I

The compounds of the formula I and their pharmaceutically acceptable salts may be made using the methods as described and exemplified in any of the following patents or applications: U.S. Pat. Nos. 6,548,493; 7,238,690; 6,552,017; 6,713,471; U.S. RE39680; U.S. RE39679; PCT/US08/03340; U.S. application Ser. No. 10/786,935; WO 2011/133224 A1, WO 2009/114181 and WO 2013/155505. If not commercially available, starting materials for these processes may be made by procedures, which are selected from the chemical art using techniques which are similar or analogous to the synthesis of known compounds. All references cited herein are hereby incorporated by reference in their entirety.

Compounds of Formula I refer to Compounds of Formula I or any of the compounds described in Methods 1.1-1.50, which include:

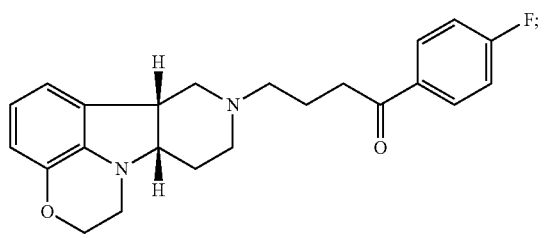

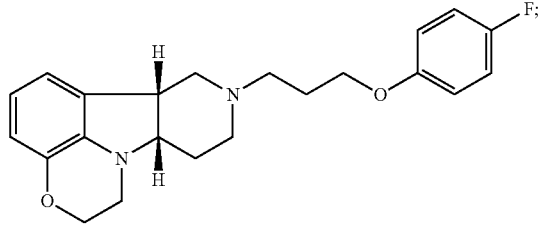

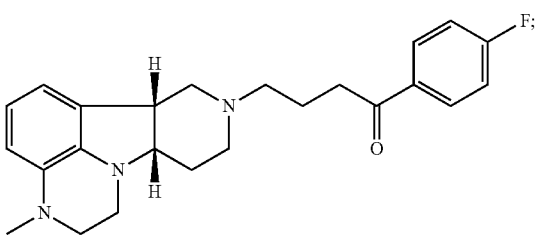

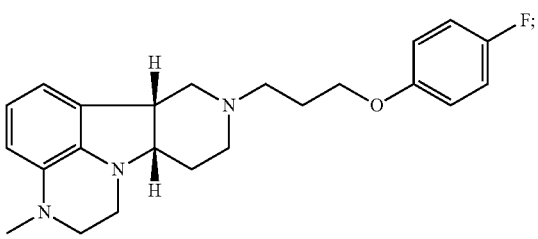

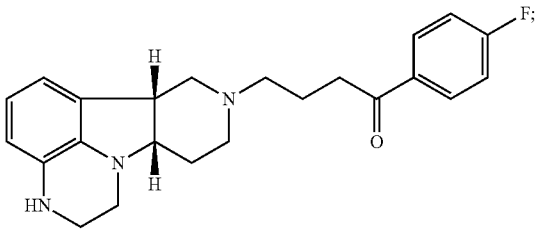

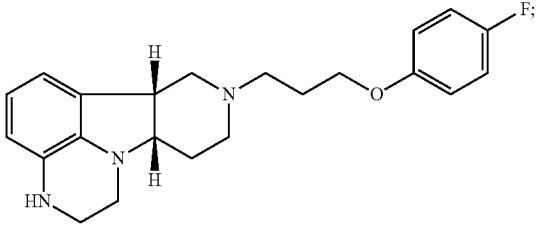

in free or pharmaceutically acceptable salt form. The Compounds of Formula I also include other specific compounds wherein Y is —C(H)(OH)— or —C(H)(OR$_1$)— wherein $R_1$ is previously defined and X is —O—, —N(H)—, or —N(CH$_3$)—. These include, for example:

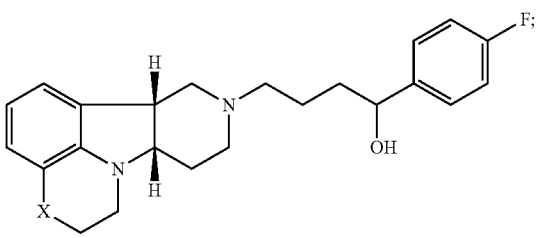

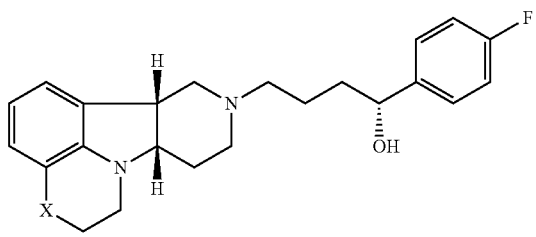

-continued

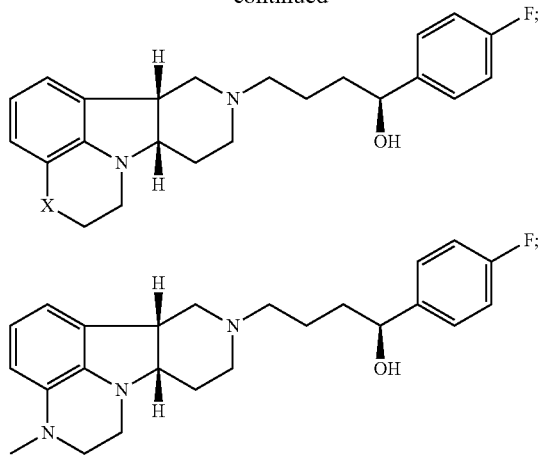

in free or pharmaceutically acceptable salt form. A specific Compound of Formula I also includes Compound A which is the compound of Formula I wherein X is —N(CH₃)— and Y is —C(O)—. The terms "Compounds of Formula I" and "Compounds of Formula I" may be used interchangeably and may be used as a sole therapeutic agent, or they may also be used in combination or for co-administration with other active agents. Also, in the methods of the present invention the phrase "a compound of Formula I" may include more than one of the compounds of Formula I.

Compounds of Formula I may in some cases also exist in prodrug form. A prodrug form is compound which converts in the body to an active Compound of Formula I. The term "pro-drug" is an art recognized term and refers to a drug precursor prior to administration that generates or releases the active metabolite in vivo following administration, via some chemical or physiological process. For example when the Compounds of Formula I contain hydroxy or carboxy substituents, these substituents may form physiologically hydrolysable and acceptable esters. As used herein, "physiologically hydrolysable and acceptable ester" means esters of Compounds of Formula I which are hydrolysable under physiological conditions to yield acids (in the case of Compounds of Formula I which have hydroxy substituents) or alcohols (in the case of Compounds of Formula I which have carboxy substituents) which are themselves physiologically tolerable at doses to be administered. For example, wherein Y of the compound of Formula I is —C(H)(OR₁), and R₁ is a physiologically hydrolysable and acceptable acyl for example —C(O)—C$_{1-21}$alkyl, e.g., —C(O)—C₃alkyl or —C(O)—C₉alkyl, these compounds may hydrolyze under physiological condition to yield a compound of Formula I wherein Y is —C(H)(OH) on the one hand and C$_{1-21}$alkyl-C(O)OH, e.g., C₃alkyl-C(O)OH or C₉alkyl-C(O)OH on the other hand. In particular, Compounds of Formula I, wherein Y is —O—, —C(R₂)(OH)—, —C(R₃)(OR₁) or —C(O)—; R₁ is C$_{1-6}$ alkyl (e.g., methyl) and R₂ and R₃ are H or C$_{1-6}$ alkyl (e.g., methyl) are active moieties. In contrast, Compounds of Formula I, wherein R₁ is —C(O)—C$_{1-21}$alkyl is a physiologically labile moiety, will have weak activity or no activity, but under physiological conditions will undergo hydrolysis to produce the Compounds of Formula I, R₁ is cleaved off to leave —C(R₂)(OH) or —C(R₃)(OH) and the other hydrolysis product is not toxic at relevant concentrations, e.g., at concentrations which would be provided by in vivo hydrolysis of a dosage of the prodrug compound. Under some physiological conditions, Compounds of Formula I, wherein R₁ is C$_{1-6}$ alkyl (e.g., methyl), may also under go in vivo conversion to the more active compound wherein R₁ is H, and therefore these compounds may be considered to be both active moieties and pro-drugs.

As will be appreciated the term prodrug thus embraces conventional pharmaceutical prodrug forms. Wherein a prodrug (e.g., the compound of formula (I) wherein R₁ is —C(O)—C$_{1-21}$alkyl) is used, the dosage amount is calculated based on the amount of the active Compound of Formula I, e.g., Y is —O—, —C(R₂)(OH)—, —C(R₃)(OR₁) or —C(O)—; R₁ is C$_{1-6}$ alkyl (e.g., methyl), R₂ and R₃ are H or C$_{1-6}$ alkyl (e.g., methyl), particularly the compound of formula (I) wherein Y is C(=O) or Y is C(H)(OH) in free base form or in the salt form, e.g., in toluenesulfonic acid addition salt form.

The Compounds of Formula I may comprise one or more chiral carbon atoms. The compounds thus exist in individual isomeric, e.g., enantiomeric or diastereomeric forms or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of Formula I may be a racemic mixture or they may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

The Compounds of Formula I may be included as a sustained or delayed release formulation, e.g., depot formulation, e.g., by dispersing, dissolving or encapsulating the Compounds of Formula I in a polymeric matrix as described hereinbefore in P.1-P.7, such that the Compound is continually released as the polymer degrades over time. The release of the Compounds of Formula I from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of Formula I to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxy-fatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethylene glycol copolymer or polyglycolic acid-polyethylene glycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly (lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl-(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 daltons, e.g., about 150,000 daltons, or 20,000 to 200,000 daltons, for example, 24,000 to 38,000 daltons, or about 113,000 daltons or about 159,000 daltons. For example, the PLGA polymer has a weight-average molecular weight of 24,000 to 38,000 daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by conventional methods, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e. g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e. g., poly (d, 1-lactide-co-glycolide) have a central glucose moiety having rays of linear polylactide chains.

The sustained or delayed release formulation as hereinbefore described may comprise the polymer in the form of microparticles (e.g., microspheres) or nanoparticles, or in a liquid form, with the Compounds of Formula I dispersed or encapsulated therein. "Microparticles" is meant solid particles that contain the Compounds of Formula I either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of Formula I and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of Formula I encapsulated therein. In the solvent extraction method, the Compounds of Formula I and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of Formula I encapsulated therein. Spray drying is an alternative manufacturing technique for preparing the microparticles.

Another method for preparing the microparticles of the invention is also described in both U.S. Pat. No. 4,389,330; 4,530,840, the contents of which are incorporated by reference.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of Formula I and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of Formula I incorporated in the microparticles usually ranges from about 1 wt % to about 90 wt. %, preferably 30 to 50 wt. %, more preferably 35 to 40 wt. %. By weight % is meant parts of the Compounds of Formula I per total weight of microparticle.

The sustained or delayed release formulation may comprise a pharmaceutically-acceptable diluent or carrier, such as a water miscible diluent or carrier.

In one embodiment, the sustained or delayed release formulation is a long-acting injectable formulation. In a further embodiment, the long-acting injectable is formulated using polymeric microspheres, e.g., microspheres comprising a PLGA matrix with Compounds of Formula I in free or pharmaceutically acceptable salt form dispersed, dissolved or encapsulated therein. In a preferred embodiment, the PLGA polymer is about 75:25 PLA/PLG (lactide:glycolide) with either carboxylic acid or carboxylic ester end groups. In a preferred embodiment, the Compound of Formula I is present in the microsphere as its free base. The microspheres may be prepared using methods known in the art, for example, by an emulsification-solvent evaporation method without micro-sieving, or an emulsification-solvent evaporation method with dry micro-sieving, or an emulsification-solvent evaporation method with wet micro-sieving.

The rate at which the PLGA microspheres degrades depends largely on the chosen molecular weight range of the polymer molecules and on the size of the microspheres. In one embodiment, the average molecular weight range for the PLGA polymer is 24,000 to 38,000 daltons. In another embodiment, the PLGA polymer has an average molecular weight of about 113,000 daltons. In still another embodiment, the PLGA polymer has an average molecular weight of about 159,000 daltons. In some embodiments, the time frame for complete degradation of the microspheres and release of the encapsulated drug compounds is, e.g., less than 6 months, less than 4 months, less than 3 months, less than 2 months, or less than 1 month.

The diameter of the microspheres, e.g., the average diameter (or $D_{50}$), the $10^{th}$ percentile diameter ($D_{10}$), the $25^{th}$ percentile diameter ($D_{25}$), the $75^{th}$ percentile diameter ($D_{75}$), or the $90^{th}$ percentile diameter ($D_{90}$), can be from about 1 µm to about 100 µm, or about 2 µm to about 80 µm, or from about 2 µm to about 60 µm, or about 2 µm to about 50 µm, or about 2 µm to about 40 µm, or about 2 µm to about 30 µm, or about 5 µm to about 35 µm, or from about 5 µm to about 25 µm, or from about 5 µm to about 20 µm, or from about 10 µm to about 20 µm, or about 10 µm to about 200 µm, from about 20 µm to about 160 µm, or from about 20 µm to about 120 µm, or from about 20 µm to about 100 µm, or from about 20 µm to about 80 µm, or from about 20 µm to about 70 µm, or from about 20 µm to about 60 µm, or from about 20 µm to about 50 µm, or from about 20 µm to about 40 µm, or from about 20 µm to about 30 µm, or from about 25 µm to about 70 µm, or from about 25 µm to about 60 µm, or from about 25 µm to about 50 µm, or from about 25 µm to about 40 µm, or from about 30 µm to about 60 µm, or from about 30 to 50 µm, or from about 30 µm to about 40 µm, or from about 30 µm to about 120 µm, or from about 40 µm to about 120 µm, or from about 40 µm to about 100 µm, or from about 40 µm to about 80 µm, or from about 40 µm to about 70 µm, or from about 40 µm to about 60 µm, or from about 40 µm to about 50 µm, or from about 50 µm to about 100 µm, or from about 50 µm to about 80 µm, or from about 50 µm to about 70 µm, or from about 50 µm to about 60 µm, or from about 60 µm to about 100 µm, or from about 60 µm to about 90 µm, or from about 60 µm to about 80 µm, or from about 60 µm to about 70 µm, or from about 70 µm to about 100 µm, or from about 70 µm to about 90 µm, or from about 70 µm to about 80 µm, or from about 75 µm to about 110 µm, or from about 40 µm to about 160 µm, or from about 50 µm to about 160 µm, or from about 50 µm to about 120 µm, or about 20 µm, about 30 µm, about 40 µm, about 50 µm, about 60 µm, about 70 µm, about 80 µm, about 90 µm, or about 100 µm. Such particle size measurements can be made, for example, using photomicroscopy, scanning electron microscopy, laser diffraction, light scattering, and other techniques known to those skilled in the art.

The amount of drug encapsulated in each microsphere, on average, can be from about 5% by weight to about 50% by weight, for example, 10% by weight to about 50% by weight, or from about 20% by weight to about 40% by weight, or from about 30% by weight to about 35% by weight, or about 8.5% by weight, or about 16% by weight, or about 30% by weight, or about 35% by weight, or about 40% by weight. In a preferred embodiment, the amount of drug encapsulated in each microsphere is about 8.5% by weight or about 16% by weight.

Details of Osmotic-controlled Release Oral delivery System composition may be found in EP 1 539 115 (U.S. Pub. No. 2009/0202631) and WO 2000/35419, the contents of each of which are incorporated by reference in their entirety.

A "therapeutically effective amount" is any amount of the Compounds of Formula I which, when administered to a subject suffering from a disease or disorder, is effective to cause a reduction, remission, or regression of the disease or disorder over the period of time as intended for the treatment.

Figure 2:
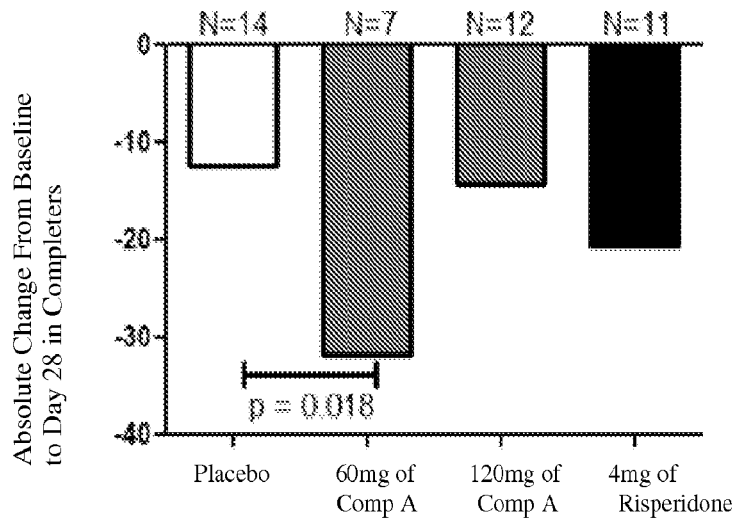
FIG. 2: Total PANSS in sub-group of patients with depression at baseline.
Figure 3:
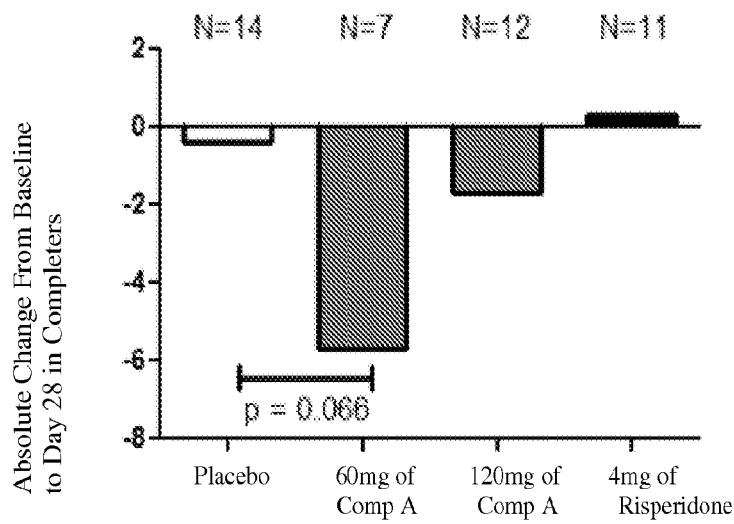
FIG. 3: PANSS Negative Symptom Sub-Scale in subgroup of patients with depression at baseline.

Depression is estimated to occur in 50% of schizophrenic patients. Schizophrenia patients with co-morbid depression, when compared to patients with only schizophrenia, generally have worse overall mental and physical health, lower quality of life, greater impairment of social relationships, less satisfaction with sleep, ability to perform daily activities, capacity for work, transportation, social support and self-esteem. Therefore, depressive symptoms exacerbate deficits in psychosocial functioning and heighten risk for psychotic relapse. Unlike dopamine receptor antagonists, Compounds of Formula I, particularly Formula A as defined in Example 1 normalize brain dopamine activity, particularly in the prefrontal cortex. The Compounds of Formula I, particularly Formula A as defined in Example 1, bind to 5-$HT_{2A}$ and dopamine $D_2$ receptors. In addition, the compounds of Formula I also modulate glutamatergic phosphoprotein ($D_1$/$GluN_{2B}$) and dopamine phosphoprotein (DPPM). Compounds of Formula I also exhibit nanomolar binding affinity for the serotonin transporter compared to known antidepressants. Therefore, in addition to treating acute symptoms (e.g., hallucinations and delusions) and residual symptoms, the compounds of Formula I are also useful for the treatment of depression and/or sleep disorders. For schizophrenic patients who also suffer from depression, the Compounds of Formula I are particularly useful for improving total PANSS and negative symptoms. While one of the atypical antipsychotic drugs, risperidone, is also useful for treating some negative symptoms, this compound is less effective compared to the sub-group of patients with depression at the baseline treated with the Compound of Formula I (See FIGS. 2 and 3 and Example 1). Therefore, in certain embodiments, the methods of the current invention are particularly useful for the treatment of depression and/or sleep disorders in patients suffering from acute and/or residual symptoms of psychosis as well as for the treatment of acute and/or residual symptoms of psychosis in patients suffering from depression and/or sleep disorders.

In a further embodiment, the invention provides a method of treating residual symptoms by administering the compound of Formula I in combination with one or more other therapeutic agents such as antipsychotic agent(s) and/or anti-depressive agent(s) and/or hypnotic agents. In such methods, the antipsychotic and/or anti-depressive and/or hypnotic agents may be an adjunct to the compound of Formula I or the compound of Formula I may be an a to the antipsychotic agent and/or anti-depressive agent and/or hypnotic agent. As used herein the term "adjunctive" or "adjunct" refers to any treatment that is used in conjunction with another to increase the chance of cure, or to increase the first treatment's efficacy. In other words, adjunctive therapy acts as an aid to the primary treatment. In another embodiment, the compound of formula I is used as a mono-therapy to treat acute symptoms and/or residual symptoms of schizophrenia as well as depression and/or sleep disorders (e.g., insomnia) in patients suffering from schizophrenia.

Other therapeutic agents which can be optionally administered to a patient in need thereof include compounds that modulate GABA activity (e.g., enhances the activity and facilitates GABA transmission), a GABA-B receptor agonist, a 5-HT modulator (e.g., a 5-$HT_{1A}$ receptor agonist, a 5-$HT_{2A}$ receptor antagonist, a 5-$HT_{2A}$ receptor inverse agonist, etc.), a melatonin receptor agonist, an ion channel modulator (e.g., blocker), a serotonin-2 receptor antagonist/reuptake inhibitor (SARIs), an orexin receptor antagonist, an H3 receptor agonist, a noradrenergic receptor antagonist, a galanin receptor agonist, a CRH receptor antagonist, human growth hormone, a growth hormone receptor agonist, estrogen, an estrogen receptor agonist, a neurokinin-1 drug, and antipsychotic agents, e.g., atypical antipsychotic agents, in free or pharmaceutically acceptable salt form.

The term "GABA" refers to gamma-aminobutyric acid. The GABA compounds are compounds which bind to the GABA receptor, and include, but are not limited to one or more of doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals) or estazolam.

Other optional therapeutic agents are 5$HT_{2A}$ receptor antagonists such as ketanserin, risperidone, eplivanserin, volinanserin (Sanofi-Aventis, France), pruvanserin, pimavanserin (ACP-103), MDL 100907 (Sanofi-Aventis, France), HY10275 (Eli Lilly), APD125 (Arena Pharmaceuticals, San Diego, Calif.), or AVE8488 (Sanofi-Aventis, France).

Still other optional therapeutic agents include pizotifen.

Other optional therapeutic agents are 5$HT_{1A}$ receptor agonists such as repinotan, sarizotan, eptapirone, buspirone or MN-305 (MediciNova, San Diego, Calif.).

Other optional compounds are melatonin receptor agonists such as melatonin, ramelteon (ROZEREM®, Takeda Pharmaceuticals, Japan), VEC-162 (Vanda Pharmaceuticals, Rockville, Md.), PD-6735 (Phase II Discovery or agomelatine.

Other optional therapeutic agents are ion channel blockers such as lamotrigine, gabapentin or pregabalin.

Other optional therapeutic agents are orexin receptor antagonists such as orexin, a 1,3-biarylurea, SB-334867-a (GlaxoSmithKline, UK), GW649868 (GlaxoSmithKline) or a benzamide derivative, for example.

Other optional therapeutic agents are serotonin-2 receptor antagonist/reuptake inhibitors (SARI) such as Org 50081 (Organon-Netherlands), ritanserin, nefazodone, serzone or trazodone.

Other optional therapeutic agents are neurokinin-1 drugs such as Casopitant (GlaxoSmithKline).

Specific examples of additional therapeutic agents include modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenlzine sulfate, protriptyline, sertraline, tranylcypromine, trazodone, trimipramine, velafaxine, chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, cariprazine, amisulpride, zotepine, sertindole, in free or pharmaceutically acceptable salt form.

The combination compositions of the invention can include mixtures of the combined drugs, as well as two or more separate compositions of the drugs, which individual compositions can be, for example, co-administered together to a patient at the same of different times.

In another aspect, the invention provides use of the Compound of Formula I or any of the pharmaceutical compositions described hereinbefore (Compositions P.1-P.7 and Compositions 2, and 2.1-2.17) comprising the Compound of Formula I in free or pharmaceutically acceptable salt form as described in Methods A or 1.1-1.50, wherein the compound is in admixture with an antioxidant. In a preferred embodiment, long acting injectable microsphere formulations of the present invention contain an antioxidant. In some embodiments, the antioxidant is a water soluble antioxidant (e.g., ascorbic acid, lipoic acid), while in other embodiments, the antioxidant is a lipid-soluble antioxidant (e.g., lipoic acid, vitamin E, tocopherols, carotenes, and phenolic antioxidants). In some embodiments, the antioxidant is a neutral or weakly basic antioxidant. Other possible antioxidants include catalytic antioxidants (e.g., ebselen) and metal-containing antioxidants. In a preferred embodiment, the antioxidant is a phenolic antioxidant, such as butylated hydroxytoluene (BHT) or butylated hydroxyanisole (BHA). In a more preferred embodiment, the antioxidant is BHT.

Dosages employed in practicing the present invention will of course vary depending, for example, on the particular disease or condition to be treated, the particular Compound of Formula I used, the mode of administration, and the therapy desired. Unless otherwise indicated, an amount of the Compound of Formula I for administration (whether administered as a free base, prodrug or as a salt form) refers to or is based on the amount of the Compound of Formula I in free base form (i.e., the calculation of the amount is based on the free base amount). In a particular embodiment, however, the dosage of the Compound of Formula I is administered based on the amount of the salt form, e.g., the toluenesulfonic acid addition salt form. Compounds of Formula I may be administered by any suitable route, including orally, parenterally or transdermally, but are preferably administered orally. As a monotherapy, the compound of Formula I may be administered at about 1 mg to 120 mg per day or 10 mg to 120 mg per day, or 10 mg to 60 mg per day, or 10 mg to 40 mg per day, or 1 mg to 10 mg per day, or 10 mg per day, 20 mg per day, 40 mg per day or 60 mg per day, preferably about 60 mg of the compound in toluenesulfonic acid addition salt form per day. Wherein 120 mg is administered, it is preferably administered at night time.

As a long-acting injectable microsphere formulation, the dosage of the Compound of Formula I depends on both the average loading of drug within the microspheres (expressed as % w/w) and on the dosage of microspheres administered (mg/kg). As a monotherapy, the Compound of Formula I may be administered as microspheres to provide a dosage of 1 to 50 mg/kg of the Compound of Formula I, for example, 5 to 25 mg/kg, preferably 5-10 mg/kg, for example about 5 mg/kg. A dose of about 5 mg/kg of the compound of Formula I can be provided, for example, by employing a dose of 60 mg/kg of microspheres, wherein each microsphere contains on average a loading of about 8.5% w/w of the Compound of Formula I.

The dosages of a compound of Formula I and/or the other anti-psychotic and/or anti-depressive agent of Method A can be the same as or lower than the approved dosage for the drug, the clinical or literature test dosage or the dosage used for the drug as a monotherapy. For example the daily dosage of compound of Formula I to be administered in combination with another anti-psychotic agent and/or an anti-depressive agent is about 1 mg to about 140 mg, in another embodiment about 1 mg to about 120 mg, in another embodiment about 10 mg to about 120 mg, in another embodiment about 10 mg to about 60 mg, in another embodiment about 10 mg to about 40 mg, in another embodiment about 20 mg to about 40 mg, in another embodiment about 1 mg to about 10 mg, and in still another embodiment, about 60 mg of the compound in free base or toluenesulfonic acid addition salt form. The amount of antipsychotic agent to be administered in combination with the compound of Formula I is about 0.01 mg to about 1000 mg, in another embodiment, about 0.1 mg to about 600 mg, e.g., about 1 mg to about 200 mg, e.g., about 1 mg to about 50 mg, e.g., about 1 mg to about 15 mg, e.g., about 4 mg. The amount of anti-depressive agent to be administered in combination with the compound of Formula I is about 0.01 mg to about 2000 mg, in another embodiment about 0.1 mg to about 200 mg, in another embodiment about 10 mg to about 200 mg. In a particular embodiment, the second therapeutic agent is the antipsychotic agent risperidone at a daily dose of about 2 mg to about 4 mg and the antidepressant is sertraline and the daily dosage of sertraline is between about 20 mg and 100 mg.

In a specific embodiment, the dosages of a compound of Formula I and/or the second (or third) therapeutic agents of Method A are lower than when used in a monotherapy. Therefore, in a particular embodiment, the daily dosage of a compound of Formula I is lower than 100 mg once daily, or less than 60 mg, or less than 40 mg, or less than 30 mg, or less than 20 mg, or less than 10 mg. In another preferred embodiment, the dosages of both the Compound of Formula I and the anti-psychotic agent and/or the anti-depressive agent of Method A are lower than the dosages used for the individual drugs as monotherapy. Therefore, in a particular embodiment, for example, Method A comprises administering (1) a Compound of Formula I at a dosage lower than 100 mg once daily, e.g., less than 60 mg or less than 40 mg; and/or (2) an antidepressant, for example an SSRI such as sertraline, at a daily dosage of less than 50 mg, more preferably, less than 20 mg, still more preferably, less than 10 mg, most preferably less than 6 mg; and/or (3) an antipsychotic agent, for example risperidone, at a daily dosage of less than 4 mg, in free or pharmaceutically acceptable salt form.

For the treatment of the disorders disclosed herein wherein the sustained or delayed release formulation is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. In a particular embodiment, the dosage regimen for sustained or delayed release formulation includes an initial oral immediate release dosage along with depot release so as to provide a steady-state blood level of the drug. Duration of action of the Compounds of Formula I may be controlled by manipulation of the polymer composition, i.e., the polymer:drug ratio and microparticle size. Wherein the formulation of the invention is a depot formulation, administration by injection is preferred. In a preferred embodiment, the formulation is a long-acting injectable microsphere formulation, as described hereinabove.

The compounds to be administered in the methods of the present invention can be in the form of free acid or free base or as pharmaceutically acceptable salts. The phrase "pharmaceutically acceptable salts" refers to derivatives of the above disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Preferably, the Compounds of Formula I are in a toluenesulfonic acid addition salt form.

The pharmaceutically acceptable salts of the compounds to be used in the methods of the invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media such as diethyl ether, ethyl acetate, ethanol, isopropanol, or acetonitrile are preferred. Further details for the preparation of these salts, e.g., toluenesulfonic acid salts in amorphous or crystal form, may be found in PCT/US08/03340 (WO 2008/112280) and/or WO 2009/114181 and WO 2011/133224.

Pharmaceutical compositions comprising the Compounds of Formula I may be prepared using conventional diluents or excipients and techniques known in the galenic art. For example the compounds can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For immediate release formulation, the compound of Formula I, in free or pharmaceutically acceptable salt form as hereinbefore described may be formulated with a pharmaceutically acceptable diluents or carrier. For sustained or delayed release formulation, the compound of the compound of Formula I, in free or pharmaceutically acceptable salt form as hereinbefore described may be formulated as hereinbefore described in any of Compositions P.1-P.7.

In a particular embodiment, the Compound of Formula I is formulated in a capsule as follows:

| Composition | % w/w | Placebo |
|---|---|---|
| 60 mg Compound of Formula I wherein X is —N(CH$_3$)— and Y is —C(O)— in toluene sulfonic acid addition salt form; | 20 | 0 |
| Mannitol (Perlitol ® 100SD NF) | 73.7 | 73.7 |
| Croscarmellose Na | 5 | 5 |
| Glyceryl Monostearate | 1 | 1 |
| Imperial Talc 500 | 0.3 | 0.3 |

For buccal administration the composition may take the form of tablets or lozenges formulated in conventional manner.

The Compounds of Formula I may be formulated for parenteral administration by injection, including using conventional catheterization techniques or infusion. Formulations for injection may be presented in unit dosage form, e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The Compounds of Formula I may also be formulated in rectal compositions such as suppositories or retention enemas, e.g., containing conventional suppository bases such as cocoa butter or other glycerides.

For intranasal administration or administration by inhalation, the Compounds of Formula I are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch. When aqueous suspensions and/or elixirs are desired for oral administration, the essential active ingredient(s) therein may be combined with various sweetening, or flavoring agents, coloring matter or dyes and, if so desired, emulsifying and/or suspending agents as well, together with such diluents as water, ethanol, propylene glycol, glycerin and various like combinations thereof.

All of the references cited hereinbefore are hereby incorporated in reference in their entirety.

The following example is to illustrate the invention but should not be interpreted as a limitation thereon.

EXAMPLE 1

Treatment of Acute as Well as Residual Symptoms of Schizophrenia

For purposes of this example, Compound A refers to the compound of Formula I wherein X is —N(CH$_3$)— and Y is —C(O)—; tosylate salt unless otherwise indicated. A randomized, double-blind, placebo-controlled, in-patient trial is performed. Four treatment arms, 4-week treatment duration, QAM dosing are performed as follows: 60 mg of Compound A; 120 mg of Compound A; positive control (4 mg Risperidone); and placebo. The primary outcome is measured by the change from baseline on Positive and Negative Syndrome Scale (PANSS) Total Score at Day 28. Secondary measures explore key differentiating features.

60 mg Compound A Treatment Arm receives 60 mg of Compound A once daily for 28 days. 120 mg Compound A Treatment Arm receives 60 mg Compound A on Study Day 1 followed by 120 mg Compound A once daily for 27 days. Risperidone Treatment Arm receives 2 mg risperidone on Study Day 1 followed by 4 mg risperidone once daily for 27 days. Placebo Treatment Arm receives placebo once daily for 28 days. All doses are administered in the morning with breakfast.

Key inclusion criteria: Clinical diagnosis of schizophrenia according to DSM-IV-TR is confirmed by modified SCID-CT. Screening Brief Psychiatric Reading Scale (BPRS) score of 40 or greater (18-items scored 1-7 each). Minimum score of 4 or higher on at least two of the following positive items: suspiciousness, conceptual disorganization, hallucinatory behavior, unusual thought content. Current exacerbated episode lasts no longer than 4 weeks. Sufficient history and/or independent reporter must verify that current state is an exacerbated state for the individual. Prior response to antipsychotic therapy within the last 5 years, defined as clinically significant and documented decrease in delusions and/or hallucinations during a documented exacerbated episode (and at least 3 months prior exposure to antipsychotic therapy).

The trial has a high subject completion rate (74%) compared to an average of 62% completion rate in other 4-week antipsychotic trials. 19% discontinues during the study treatment period (during Day 1-28). 7% completes study treatment through Day 28, but are lost to follow up. At 60 mg, the trial shows that Compound A demonstrates antipsychotic efficacy on primary endpoint total PANSS change from baseline at Day 28:

TABLE 1

| Treatment Arm (N/arm) | LS Mean Change from Baseline on Day 28 Total PANSS (±SE) using MMRM/ITT | LS Mean Difference from Placebo | p-value | Effect Size |
|---|---|---|---|---|
| Placebo (N = 80) | −7.4 ± 1.7 | n/a | n/a | n/a |
| 60 mg Compound A (N = 76) | −13.2 ± 1.7 | −5.8 | 0.017 | 0.4 |
| 120 mg Compound A (N = 80) | −8.3 ± 1.7 | −0.9 | 0.708 | 0.1 |
| 4 mg Risperidone (N = 75) | −13.4 ± 1.7 | −6.0 | 0.013 | 0.4 |

For patients with prominent negative symptoms at baseline (e.g., patients with a score of 4 or higher on at least 3 negative symptom items at baseline), 60 mg of Compound A improves negative symptoms qualitatively (see FIG. 1).

In a subgroup of patients with symptoms of depression that are secondary to schizophrenia measured by the cut-off score for depression (Calgary Depression Scale for Schizophrenia, CDSS, score >6) at baseline (which accounts for approximately 16% of the patients in the study), 60 mg of Compound A significantly reduces depression as measured by the CDSS (p=0.044). Compound A at 60 mg also robustly improves total PANSS (See FIG. 2) and negative symptoms (See FIG. 3).

Figure 4:
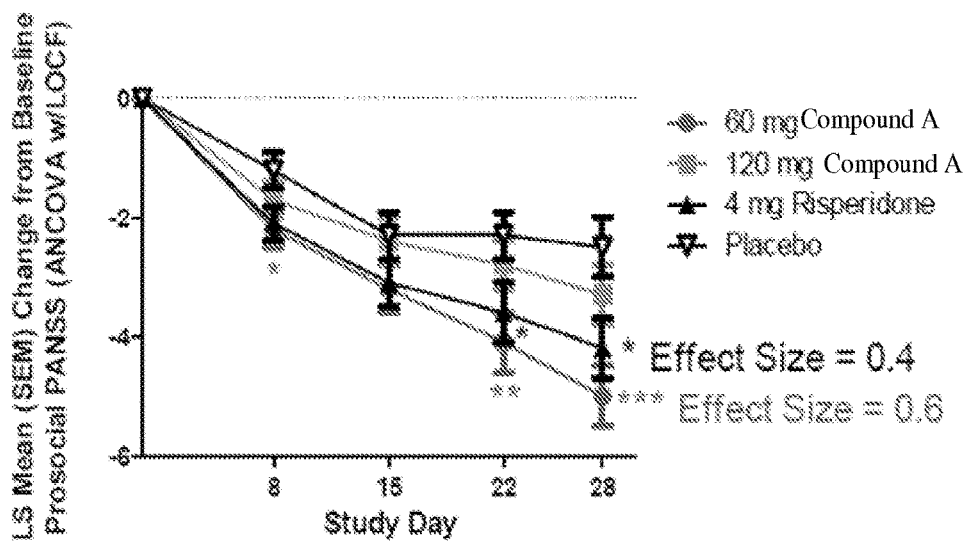
FIG. 4: Prosocial PANSS Factor Change from Baseline compared to Placebo.

At 60 mg, Compound A is also shown to significantly improve the Prosocial PANSS Factor change from baseline compared to placebo (See FIG. 4).

EXAMPLES 2-10

Preparation of Long-Acting Injectable Microsphere Formulations

EXAMPLE 2

Preparation of the PLGA (PLA/PLG=75/25, 0.32-0.44 dl/g) Microspheres of Compound a Free Base (Lot A)

For purposes of Examples 2-10, Compound A refers to the compound of Formula I wherein X is —N(CH$_3$)— and Y is —C(O)— in free base form.

2 g of Poly(vinyl alcohol) (PVA, 87-89% hydrolyzed, typical molecular weight 13,000-23,000) in 400 mL of deionized water is sonicated in a bath sonicator for 5-10 min and then filtered to give 0.5% PVA aqueous solution. The filtrate is transferred to a 500 mL flat bottom flask. 0.80 g of Compound A and 1.2 g of PLGA polymer (PLA/PLG=75/25, 0.32-0.44 dl/g, acid end groups) are dissolved in 15 mL of dichloromethane. This solution is added into the 0.5% PVA aqueous solution dropwise with vigorous stirring. A mechanical overhead stirrer is used and the stirring speed is around 700 ppm during the addition. After the completion of the addition, the mixture is stirred at this speed for an hour and then stirred at approximately 550 ppm for 4 hours. An argon stream is applied throughout the process to promote the evaporation of dichloromethane from the aqueous solution. A size 75 μm microsieve is stacked on the top of a 20 μm microsieve. The suspension is slowly poured onto the stacked microsieves and then washed with water at least five times. The microspheres collected on the 20 μm microsieve is transferred into a 50 mL falcon tube with deionized water and then lyophilized to give 1.43 g of Compound A PLGA microspheres with a size distribution of 20-60 μm. The drug content in the obtained microspheres is 37.5%, as determined by HPLC. The initial loading for this preparation is 40% (calculated based upon 0.8 g of Compound A free base in 1.2 g of the PLGA polymer). Drug entrapment efficiency is 93.8%.

EXAMPLE 3

Preparation of the PLGA (PLA/PLG=75/25, 0.32-0.44 dl/g) Microspheres of Compound A Free Base (Lot B)

This lot of Compound A PLGA microspheres is prepared using a procedure similar to the one described in Example 2 except that sterilized water is used in the whole process instead of deionized water and all labwares in touch with microspheres are sterilized. 1.49 g of Compound A PLGA microspheres with a size distribution of 20-50 μm are obtained. The drug content in the obtained microspheres is 38%, as determined by HPLC. The initial drug loading for this lot is 40% and drug entrapment efficiency is 85.8%.

EXAMPLE 4

Preparation of the PLGA (PLA/PLG=75/25, 0.89 dl/g) Microspheres of Compound A Free Base (Lot C)

2 g of Poly(vinyl alcohol) (PVA, 87-89% hydrolyzed, typical molecular weight 13000-23000) in 400 mL of sterilized water is sonicated in a bath sonicator for 5-10 min and then filtered to give 0.5% PVA aqueous solution. The filtrate is transferred to a 500 mL flat bottom flask. 0.80 g of Compound A and 1.2 g of PLGA polymer (PLA/PLG=75/25; 0.89 dl/g; MW: 159,000 d; ester end groups) are dissolved in 16 mL of dichloromethane with sonication. This solution is added into the 0.5% PVA aqueous solution dropwise with vigorous stiffing. A mechanical overhead stirrer is used and the stirring speed is ~700 ppm during the addition. After the completion of the addition, the mixture is stirred at this speed for an hour and then stirred at approximately 550 ppm for 4 hours. An argon stream is applied throughout the process to promote the evaporation of dichloromethane from the aqueous solution. A size 75 μm microsieve is stacked on the top of a 20 μm microsieve. The suspension is slowly poured onto the stacked microsieves and then washed with water at least five times. The microspheres collected on the 20 μm microsieve is transferred into a 50 mL falcon tube with deionized water and then lyophilized to give 0.78 g of Compound A PLGA microspheres with a size distribution of 20-70 μm. The drug content in the obtained microspheres is 36%, as determined by HPLC. The initial loading for this preparation is 40% (calculated based upon 0.8 g of Compound A free base in 1.2 g of the PLGA polymer). Drug entrapment efficiency is 90%.

EXAMPLE 5

Preparation of the PLGA (PLA/PLG=75/25, 0.68 dl/g) Microspheres of Compound A Free Base (Lot D)

This lot of Compound A PLGA microspheres is prepared using a procedure similar to the one described in Example 4 except that a new type of PLGA polymer (PLA/PLG=75/25; 0.68 dl/g; MW: 113,000 d; acid end groups) is used in the microsphere preparation. 1.11 g of Compound A PLGA microspheres with a size distribution of 25-75 μm are obtained. The drug content in the obtained microspheres is 36%, as determined by HPLC. The initial drug loading for this lot is 40% and drug entrapment efficiency is 90%.

EXAMPLE 6

Preparation of the PLGA (PLA/PLG=75/25, 0.68 dl/g) Microspheres of Compound A Free Base (Lot E)

This lot of PLGA microspheres is prepared using a procedure similar to the one described in Example 4 except that a different type of PLGA polymer (PLA/PLG=75/25; 0.68 dl/g; MW: 113,000 d; acid end groups) and a microsieve with a pore size of 75 μm is used in the microsphere preparation. 0.25 g of Compound A PLGA microspheres with a size distribution of 75-110 μm are obtained. The drug content in the obtained microspheres is 37%, as determined by HPLC. The initial drug loading for this lot is 40% and drug entrapment efficiency is 93%.

EXAMPLE 7

Preparation of the PLGA (PLA/PLG=75/25, 0.68 dl/g) Microspheres of Compound A Free Base (Lot F)

This lot of Compound A PLGA microspheres is prepared using a procedure similar to the one described in Example 4 except that a new type of PLGA polymer (PLA/PLG=75/25; 0.68 dl/g; MW: 113,000 d; acid end groups) and microsieves with pore sizes of 53 μm and 106 μm, respectively, are used in the microsphere preparation. 1.22 g of PLGA microspheres with a size distribution of 52-101 μm are obtained. The drug content in the obtained microspheres is 37%, as determined by HPLC. The initial drug loading for this lot is 40% and drug entrapment efficiency is 93%.

EXAMPLE 7-A

Preparation of the PLGA (PLA/PLG=75/25, 0.32-0.44 dl/g) Microspheres of Compound A Free Base (Lot F)

2 g of Poly(vinyl alcohol) (PVA, 87-89% hydrolyzed, typical molecular weight 13000-23000) in 400 mL of sterilized water is sonicated in a bath sonicator for 5-10 min and then filtered to give 0.5% PVA aqueous solution. The filtrate is transferred to a 500 mL flat bottom flask. 0.40 g of Compound A and 2.1 g of PLGA polymer (PLA/PLG=75/25; 0.32-0.44 dl/g; acid end groups) are dissolved in 21 mL of dichloromethane with sonication. This solution is added into the 0.5% PVA aqueous solution dropwise with vigorous stirring. A mechanical overhead stirrer is used and the stirring speed is ~500 ppm during the addition. After the completion of the addition, the mixture is stirred at approximately 500 ppm for 5 hours. An argon stream is applied throughout the process to promote the evaporation of dichloromethane from the aqueous solution. A size 75 μm microsieve is stacked on the top of a 30 μm microsieve. The suspension is slowly poured onto the stacked microsieves and then washed with water at least five times. The microspheres collected on the 30 μm microsieve is transferred into a ¼ oz glass vial and then dried under vacuum to give 1.43 g of Compound A free base PLGA microspheres with a size distribution of 25-70 μm. The drug content in the obtained microspheres is 8.5%, as determined by HPLC. The initial loading for this preparation is 16% (calculated based upon 0.4 g of Compound A free base in 2.1 g of the PLGA polymer). Drug entrapment efficiency is 53%.

EXAMPLE 8

Preparation of the PLGA (PLA/PLG=75/25, 0.68 dl/g) Microspheres of Compound B Free Base (Lot G)

For purposes of this example, Compound B refers to the compound of Formula I wherein X is —N(CH$_3$)— and Y is —CH(OH)—. 2 g of Poly(vinyl alcohol) (PVA, 87-89% hydrolyzed, typical molecular weight 13000-23000) in 400 mL of deionized water is sonicated in a bath sonicator for 5-10 min and then filtered to give 0.5% PVA aqueous solution. The filtrate is transferred to a 500 mL flat bottom flask. 0.80 g of Compound B (free base) and 1.2 g of PLGA polymer (PLA/PLG=75/25, 0.32-0.44 dl/g, acid end groups) are dissolved in 15 mL of dichloromethane. This solution is added into the 0.5% PVA aqueous solution dropwise with vigorous stirring. A mechanical overhead stirrer is used and the stirring speed is around 700 ppm during the addition. After the completion of the addition, the mixture is stirred at this speed for an hour and then stirred at approximately 550 ppm for 4 hours. An argon stream is applied throughout the process to promote the evaporation of dichloromethane from the aqueous solution. A size 75 μm microsieve is stacked on the top of a 20 μm microsieve. The suspension is slowly poured onto the stacked microsieves and then washed with water at least five times. The microspheres collected on the 20 μm microsieve is transferred into a 50 mL falcon tube with deionized water and then lyophilized to give 1.36 g of Compound B PLGA microspheres with a size distribution of 13-60 μm. The drug content in the obtained microspheres is 29%, as determined by HPLC. The initial loading for this preparation is 40% (calculated based upon 0.8 g of Compound B free base in 1.2 g of the PLGA polymer). Drug entrapment efficiency is 72.5%.

EXAMPLE 9

Loading Determination of Long-Acting Injectable Microspheres

About 5 mg of microspheres are dissolved in 10 mL of a 1:2 v/v dichloromethane/acetonitrile mixture. 1 mL of the solution is transferred into 1.5 mL microtube and solvent is removed using the Savant Speed Vac; then the residue is reconstituted in 95% acetonitrile/5% water. This solution is filtered (Waters 0.2 μm Nylon syringe filter) and measurements are conducted in triplicate via Waters Acquity UPLC with a PDA UV absorbance detector set at 314 nm. The mobile phase is gradient acetonitrile-water with v/v 0.1% formic acid. Waters Acquity UPLC HSS T3 (2.1×50 mm) column is used with the flow rate at 0.3 ml/min A standard curve is prepared to include about 0.1-0.7 mg/mL of the expected Compound A concentration.

Drug loading is determined as: percent drug loading=100×(10×concentration of filtered solution)/weight of microspheres used. The results are reported as the mean±SD.

EXAMPLE 10

Drug Release Determination of Long-Acting Injectable Microspheres

Microsphere drug release experiments are carried out in 0.1 M phosphate buffer (pH 7.4) containing 10 mM ascorbic acid. Microsphere suspensions containing known amounts of drug (about 30 mg) are placed in a regenerated cellulose membrane dialysis device (Float-a-Lyzer). The Float-a-Lyzer is placed in a 45-mL falcon tube containing 40 mL buffer, the release medium maintained at 37° C. and shook horizontally at 100 rpm in an oven. The buffer is replaced with fresh solution at predetermined time intervals. The drug content of the release medium is determined via UPLC using UV-vis absorbance at 314 nm with a standard curve constructed with known concentrations of ITI07 (3-30 μg/mL).

EXAMPLE 11

Pharmacokinetics of Long-Acting Injectable Microspheres

For in vivo characterization, in vivo drug release (pharmacokinetic study) is determined. The pharmacokinetics of the formulation is studied in adult male Sprague-Dawley rats. Rats (N=12/experiment) are injected subcutaneously in the intra-scapular region with a suspension (2 ml/kg) of Compound A free base formulated in biodegradable, PLGA microspheres (about 60 mg/rat) suspended in a solution of 0.5% low viscosity carboxymethylcellulose in sterile saline containing 0.1% Tween-20. At specified times after injection (i.e., 24 hours to 28 days) rats (N=2 or 3/time point) are tested for 5-HT$_{2A}$ agonist-induced head twitch behavior as a functional indicator of 5-HT$_{2A}$ antagonist activity due to circulating Compound A levels. For these measurements rats are injected intraperitoneally with 2, 5-dimethoxy-4-iodo-amphetamine (DOI) (2.5 mg/kg) in a volume of 2 ml/kg. Five minutes later rats are observed for stereotypic head twitch behaviors which are manually counted and recorded. Rats are killed by decapitation at specified time points (i.e., 24 h-28 days after injection of the formulation) and trunk blood and brain tissue is collected for analysis of levels of Compound A and its known metabolites (Compound B), using an HPLC-MS/MS method.

Using a procedure as described or similarly described above, several long-acting injectable microsphere formulations are analyzed for their in vivo release profile of the compound of Formula I wherein X is —N(CH$_3$)— and Y is —C(O)— (Compound A free base). The results are summarized in the below tables. Table 2 shows the physical characteristics of LAI microsphere formulations 2-7 and 7A. Particle size distribution is determined using photomicroscopy.

TABLE 2

| Ex. | Molecular Weight | Inherent Viscosity (dL/g) | Initial drug content (wt/wt %) | Actual drug loading (wt/wt %) | Entrapment efficiency (%) | Size distribution (μm) |
|---|---|---|---|---|---|---|
| 2 | 24K-38K | 0.32-0.44 | 40 | 38 | 95 | 22-57 |
| 3 | 24K-38K | 0.32-0.44 | 40 | 38 | 95 | 24-48 |
| 4 | 159K | 0.89 | 40 | 36 | 90 | 28-63 |
| 5 | 113K | 0.68 | 40 | 36 | 90 | 25-73 |
| 6 | 113K | 0.68 | 40 | 37 | 93 | 75-108 |
| 7 | 113K | 0.68 | 40 | 37 | 93 | 52-101 |
| 7-A | 24K-38K | 0.32-0.44 | 16 | 8.5 | 53 | 25-69 |

Actual drug loading describes the % weight/weight of Compound A in the microspheres. Microspheres are dosed to the animals at either 60 mg/kg or 30 mg/kg. Compound A dose, in Table 2, represents the amount of drug dosed to the animal (actual drug loading x microsphere dose). Plasma and brain levels of both Compound A, and the major metabolite of Compound A (Compound B), are measured on Day 1, Day 3, Day 7, Day 10, Day 14 and Day 21 after subcutaneous injection in rats. The results are shown in Table 3.

TABLE 3

| Ex. No. | Microsphere dose (mg/kg) | Comp A dose (mg/kg) | Values are Compound A (Compound B) (ng/mL) | | | | | | | | | | | |
|---|---|---|---|---|---|---|---|---|---|---|---|---|---|---|
| | | | Day 1 plasma | Day 1 brain | Day 3 plasma | Day 3 brain | Day 7 plasma | Day 7 brain | Day 10 plasma | Day 10 brain | Day 14 plasma | Day 14 brain | Day 21 plasma | Day 21 brain |
| 2 | 60 | 22.8 | 31 (4) | 300 (51) | 63 (59) | 154 (143) | 15 (3) | 125 (32) | 8 (*) | 78 (24) | | | | |
| 3 | 60 | 22.8 | | | 47 (38) | 170 (108) | 18 (4) | 84 (26) | | | | | 0.5 (0.4) | 4 (3) |
| 5 | 60 | 21.6 | 4 (0.5) | 41 (12) | 72 (49) | 216 (114) | 26 (23) | 127 (65) | 5 (1) | 33 (8) | | | 1 (*) | 4 (*) |
| 7 | 30 | 11.1 | 1 (1) | 13 (6) | 32 (7) | 123 (28) | 8 (2) | 18 (6) | 2 (*) | 9 (3) | | | | |
| 7-A | 60 | 5.1 | 3 (0.4) | 54 (10) | 5 (0.6) | 42 (9) | 10 (1.2) | 70 (16) | 9 (1) | 69 (12) | 4 (0.6) | 35 (8) | 1 (0.2) | 11 (4) |

It is observed, unexpectedly, that a superior release profile (prolonged release) is obtained using a lower microsphere loading. The microsphere formulation having a loading of 8.5% by weight (Ex. 7-A) yields a release profile with a peak brain level of drug at day 7, with measurable levels of drug through day 21 of the study (11 ng/mL brain level on day 21). In contrast, the microspheres with higher loading of drug result in earlier peak release of drug with no measurable levels or low levels of drug being maintained beyond day 10 of the study.

The invention claimed is:

1. A method for the treatment of residual symptoms of schizophrenia as defined in the Positive and Negative Syndrome Scale (PANSS) for Schizophrenia, comprising administering to a patient in need thereof, after treatment of acute symptoms of schizophrenia with an antipsychotic agent, an effective amount of a compound of Formula I:

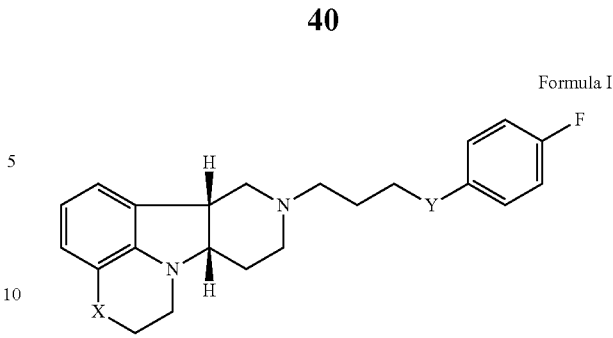

Formula I wherein:
X is —O—, —NH— or —N($CH_3$)—;
Y is —O—, —C($R_2$)(OH)—, —C($R_3$)($OR_1$) or —C(O)—; and
$R_1$ is —$C_{1-6}$alkyl or —C(O)—$C_{1-21}$alkyl, optionally saturated or unsaturated and optionally substituted with one or more hydroxyl or $C_{1-22}$alkoxy groups wherein such compound hydrolyzes to form the residue of a natural or unnatural, saturated or unsaturated fatty acid;
$R_2$ is H or —$C_{1-6}$alkyl; and
$R_3$ is H or —$C_{1-6}$alkyl;
in free or pharmaceutically acceptable salt form;
wherein the patient significantly improves on the Prosocial PANSS Factor change from baseline.

2. The method according to claim 1, wherein the compound of Formula I is a compound wherein:

X is —O—, —NH— or —N($CH_3$)—;
Y is —O—, —C(H)(OH)—, —C(H)($OR_1$) or —C(O)—; and
$R_1$ is —C(O)—$C_{1-21}$alkyl, optionally saturated or unsaturated and optionally substituted with one or more hydroxy or $C_{1-22}$alkoxy groups, wherein such compound hydrolyzes to form the residue of a natural or unnatural, saturated or unsaturated fatty acid,
in free or pharmaceutically acceptable salt form.

3. The method according to claim 1, wherein the compound of Formula I is selected from a group consisting of compounds of formula I wherein:

X is —O— and Y is —C(H)(OH)—,
X is —NH— and Y is —C(H)(OH)—,
X is —N($CH_3$)— and Y is —C(H)(OH)—,
X is —O— and Y is —C(O)—,
X is —O— and Y is —O—,
X is —N($CH_3$)— and Y is —C(O)—,
X is —N($CH_3$)— and Y is —O—,
X is —NH— and Y is —C(O)—, X is —NH— and Y is —O—,
X is —N(CH₃)— and Y is —C(H)(OR₁),
X is —NH— and Y is —C(H)(OR₁), or
X is —O— and Y is —C(H)(OR₁);
X is —O— and Y is —C(CH₃)(OH)—,
X is —NH— and Y is C(CH₃)(OH)—,
X is —N(CH₃)— and Y is C(CH₃)(OH)—.

4. The method of claim 1 wherein X is —N(CH₃)— and Y is —C(O)— or —C(H)(OH).

5. The method of claim 1 wherein said residual symptoms are selected from blunted affect, emotional withdrawal, poor rapport, passive social withdrawal, apathetic social withdrawal, difficulty in abstract thinking, lack of spontaneity and flow of conversation and stereotyped thinking; somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance; cognitive impairment and sleep disorders.

6. The method of claim 1, further comprising the administration of one or more other therapeutic agents selected from additional antipsychotic agents and/or anti-depressive agents and/or hypnotic agents.

7. The method of claim 6, wherein the one or more other therapeutic agents are selected from compounds that modulate GABA activity, a GABA-B agonist, a 5-HT modulator, a melatonin agonist, an ion channel modulator, a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug; and antipsychotic agents, in free or pharmaceutically acceptable salt form.

8. The method of claim 6, wherein the one or more other therapeutic agents are selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, velafaxine, chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, cariprazine, amisulpride, zotepine, and sertindole, in free or pharmaceutically acceptable salt form.

9. The method of claim 6, wherein the administration of the compound of Formula I is adjunct to the administration of the one or more other therapeutic agents.

10. The method of claim 6, wherein the one or more other therapeutic agents are antipsychotic agents selected from chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, cariprazine, amisulpride, zotepine, and sertindole, in free or pharmaceutically acceptable salt form.

11. The method of claim 6, wherein the administration of one or more other therapeutic agents is adjunct to the administration of the compound of Formula I.

12. The method of claim 6, wherein the one or more other therapeutic agents are anti-depressive agents selected from one or more of amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenlzine sulfate, protriptyline, sertraline, tranylcypromine, trazodone, trimipramine, and venlafaxine.

13. The method of claim 6 wherein the one or more other therapeutic agents are anti-depressive agent selected from selective serotonin reuptake inhibitors (SSRIs), serotonin-norepinephrine reuptake inhibitors (SNRIs), and tricyclic antidepressants.

14. The method of claim 13, wherein the anti-depressive agent is a SSRI.

15. The method according to claim 1 wherein the compound of Formula I is administered orally as a composition comprising a pharmaceutically acceptable diluent or carrier as an oral unit dose form that is a tablet, or capsule.

16. The method according to claim 1 wherein the effective amount of the compound of Formula I is a daily dose of about 1 mg to about 140 mg.

17. The method according to claim 1 wherein the effective amount of the compound of Formula I is a daily dose of about 10 mg to about 120 mg.

18. The method according to claim 1 wherein the effective amount of the compound of Formula I is a daily dose of about 20 mg to about 60 mg.

19. The method according to claim 1 wherein the effective amount of the compound of Formula I is a daily dose of about 20 mg, about 40 mg or about 60 mg.

20. The method of claim 1 wherein the patient has not responded adequately to treatment with another antipsychotic agent or combination of antipsychotic agents.

21. The method of claim 20, wherein the patient has not responded to treatment with one or more antipsychotic agents selected from chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, cariprazine, amisulpride, zotepine, and sertindole.

22. The method of claim 21 wherein the patient has not responded to treatment with risperidone.

23. The method according to claim 1 wherein the compound of Formula I is formulated in a sustained or delayed release formulation.

24. The method according to claim 23, wherein the sustained or delayed release formulation is a long-acting injectable microsphere formulation.

25. A method for the treatment of residual symptoms of schizophrenia as defined in the Positive and Negative Syndrome Scale (PANSS) for Schizophrenia, comprising administering, after treatment of acute symptoms of schizophrenia with an antopsychotic agent, to a patient in need thereof a long acting injectable composition comprising a PLGA matrix of 75:25 PLA/PLG with either carboxylic acid or carboxylic acid end groups, and an effective amount of a compound of Formula I:

Formula I

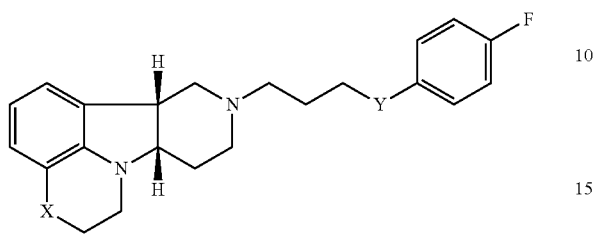

wherein:
X is —O—, —NH— or —N(CH$_3$)—;
Y is —O—, —C(R$_2$)(OH)—, —C(R$_3$)(OR$_1$) or —C(O)—; and
R$_1$ is —C$_{1-6}$alkyl or —C(O)—C$_{1-21}$alkyl, optionally saturated or unsaturated and optionally substituted with one or more hydroxy or C$_{1-22}$alkoxy groups, wherein such compound hydrolyzes to form the residue of a natural or unnatural, saturated or unsaturated fatty acid;
R$_2$ is H or —C$_{1-6}$ alkyl; and
R$_3$ is H or —C$_{1-6}$ alkyl;
in free or pharmaceutically acceptable salt form;
wherein the patient significantly improves on the Prosocial PANSS Factor change from baseline.

* * * * *

UNITED STATES PATENT AND TRADEMARK OFFICE
CERTIFICATE OF CORRECTION

PATENT NO. : 9,956,227 B2  
APPLICATION NO. : 15/101874  
DATED : May 1, 2018  
INVENTOR(S) : Vanover et al.

Page 1 of 1

It is certified that error appears in the above-identified patent and that said Letters Patent is hereby corrected as shown below:

On Sheet 1, in the X-axis of Figure 1, the label:
"Effect Size 0.45
Comp A"
Should be replaced with the label:
-- 60mg of
Comp A --

On Sheet 1, in the X-axis of Figure 1, the label:
"20mg of
Comp A"
Should be replaced with the label:
-- 120mg of
Comp A --

Signed and Sealed this
Fourth Day of September, 2018

Andrei Iancu
*Director of the United States Patent and Trademark Office*